United States Patent
Miao et al.

(10) Patent No.: US 11,311,334 B2
(45) Date of Patent: *Apr. 26, 2022

(54) SYSTEM FOR LASER ABLATION SURGERY

(71) Applicant: Verily Life Sciences LLC, Mountain View, CA (US)

(72) Inventors: Xiaoyu Miao, Palo Alto, CA (US); Hao Du, San Jose, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 16/560,191

(22) Filed: Sep. 4, 2019

(65) Prior Publication Data
US 2020/0000521 A1 Jan. 2, 2020

Related U.S. Application Data

(63) Continuation of application No. 14/282,989, filed on May 20, 2014, now Pat. No. 10,420,608.

(51) Int. Cl.
*A61B 18/20* (2006.01)
*A61B 5/01* (2006.01)
(Continued)

(52) U.S. Cl.
CPC .............. *A61B 18/20* (2013.01); *A61B 5/015* (2013.01); *A61B 18/203* (2013.01);
(Continued)

(58) Field of Classification Search
None
See application file for complete search history.

(56) References Cited

U.S. PATENT DOCUMENTS 5,049,147 A * 9/1991 Danon ................... A61B 18/20
606/10
5,074,862 A 12/1991 Rausis
(Continued)

FOREIGN PATENT DOCUMENTS

| WO | 0126591 A1 | 4/2001 |
| WO | 0178830 A2 | 10/2001 |
| WO | 2014043201 A1 | 3/2014 |

OTHER PUBLICATIONS

International Search Report and Written Opinion of International Application No. PCT/US2015/030562, dated Aug. 7, 2015.
(Continued)

*Primary Examiner* — Carl H Layno
*Assistant Examiner* — Manolis Pahakis
(74) *Attorney, Agent, or Firm* — McDonnell Boehnen Hulbert & Berghoff LLP

(57) ABSTRACT

An active tracking system includes an imager configured to image the temperature of a biological tissue and a heating laser configured to heat regions of the biological tissue. The imager locates high-temperature regions of the biological tissue and the heating laser is controlled to point toward target regions of the biological tissue based on the located high-temperature regions. The active tracking system can be used to control a heating laser to continuously heat a target region of a biological tissue even when the target region moves relative to the heating laser. The active tracking system could allow one or more target regions of a biological tissue to be 'tagged' with heat by the heating laser and to be tracked even when the one or more target regions move relative to the heating laser. Devices and methods for operating such active tracking systems are also provided.

11 Claims, 6 Drawing Sheets

(51) Int. Cl.
*A61B 5/00* (2006.01)
*A61B 18/00* (2006.01)
*A61N 5/06* (2006.01)
*A61B 17/00* (2006.01)
*A61N 5/067* (2006.01)

(52) U.S. Cl.
CPC .............. *A61B 5/0059* (2013.01); *A61B 5/01* (2013.01); *A61B 2017/00084* (2013.01); *A61B 2018/00642* (2013.01); *A61B 2018/00779* (2013.01); *A61B 2018/00791* (2013.01); *A61B 2018/20359* (2017.05); *A61N 5/067* (2021.08); *A61N 2005/0626* (2013.01)

(56) References Cited

U.S. PATENT DOCUMENTS

| | | | |
|---|---|---|---|
| 5,165,410 A * | 11/1992 | Warne | A61B 6/00 250/363.04 |
| 5,219,347 A * | 6/1993 | Negus | A61B 18/201 606/17 |
| 5,364,390 A | 11/1994 | Taboada et al. | |
| 5,620,436 A | 4/1997 | Lang et al. | |
| 5,829,444 A * | 11/1998 | Ferre | A61B 90/14 128/897 |
| 5,868,731 A | 2/1999 | Budnik et al. | |
| 6,156,030 A | 12/2000 | Neev | |
| 6,165,170 A * | 12/2000 | Wynne | A61B 18/203 606/9 |
| 6,190,377 B1 | 2/2001 | Kuzdrall | |
| 6,293,940 B1 | 9/2001 | Slatkine | |
| 6,442,419 B1 * | 8/2002 | Chu | A61B 5/015 250/316.1 |
| 6,533,774 B1 | 3/2003 | Ota | |
| 6,542,767 B1 | 4/2003 | McNichols et al. | |
| 6,615,071 B1 | 9/2003 | Casscells, III et al. | |
| 6,676,654 B1 | 1/2004 | Balle-Petersen et al. | |
| 6,932,807 B1 * | 8/2005 | Tomita | A61F 9/008 606/10 |
| 6,984,228 B2 | 1/2006 | Anderson et al. | |
| 6,996,256 B2 * | 2/2006 | Pavlidis | A61B 5/015 382/118 |
| 7,044,602 B2 * | 5/2006 | Chernyak | A61B 3/1015 351/208 |
| 7,066,929 B1 | 6/2006 | Azar et al. | |
| 7,469,160 B2 * | 12/2008 | Banks | A61B 5/0059 600/123 |
| 7,657,303 B2 * | 2/2010 | Mate | A61B 34/20 600/424 |
| 7,699,838 B2 | 4/2010 | Breen et al. | |
| 8,027,710 B1 * | 9/2011 | Dannan | A61B 1/313 600/407 |
| 8,048,065 B2 * | 11/2011 | Grecu | G06K 9/00597 606/10 |
| 8,155,416 B2 | 4/2012 | Nields et al. | |
| 8,764,736 B2 * | 7/2014 | Kurtz | A61F 9/008 606/4 |
| 9,153,034 B2 * | 10/2015 | Mostafavi | A61B 6/52 |
| 9,272,161 B2 * | 3/2016 | Gertner | A61N 5/1001 |
| 9,433,350 B2 * | 9/2016 | Schonborn | A61B 5/418 |
| 9,486,128 B1 * | 11/2016 | Hannaford | A61B 5/0071 |
| 9,833,254 B1 * | 12/2017 | Barral | A61B 17/02 |
| 9,895,063 B1 * | 2/2018 | Hannaford | A61B 5/061 |
| 10,178,959 B1 * | 1/2019 | Homyk | A61B 5/6824 |
| 10,420,608 B2 * | 9/2019 | Miao | A61B 18/20 |
| 10,624,663 B1 * | 4/2020 | Barral | A61B 34/32 |
| 2001/0053907 A1 * | 12/2001 | Ota | A61B 18/203 606/10 |
| 2002/0049432 A1 | 4/2002 | Mukai | |
| 2002/0052547 A1 * | 5/2002 | Toida | A61B 1/00096 600/425 |
| 2002/0077542 A1 * | 6/2002 | Vilsmeier | A61B 34/20 600/424 |
| 2002/0118170 A1 | 8/2002 | Iaria et al. | |
| 2002/0151778 A1 | 10/2002 | Dowlatshahi | |
| 2003/0032950 A1 | 2/2003 | Altshuler et al. | |
| 2003/0164172 A1 * | 9/2003 | Chumas | A61B 90/13 128/898 |
| 2003/0195592 A1 | 10/2003 | Black | |
| 2003/0208189 A1 * | 11/2003 | Payman | A61F 9/008 606/5 |
| 2005/0085718 A1 * | 4/2005 | Shahidi | A61B 8/0833 600/424 |
| 2005/0143793 A1 * | 6/2005 | Korman | A61N 5/0616 607/94 |
| 2005/0283058 A1 * | 12/2005 | Choo-Smith | A61B 5/0066 600/315 |
| 2005/0285595 A1 * | 12/2005 | Green | G01R 33/3806 324/307 |
| 2006/0052661 A1 | 3/2006 | Gannot et al. | |
| 2006/0116669 A1 | 6/2006 | Dolleris | |
| 2007/0055140 A1 | 3/2007 | Kuroda | |
| 2008/0033410 A1 * | 2/2008 | Rastegar | A61B 18/20 606/9 |
| 2008/0091249 A1 | 4/2008 | Wang | |
| 2008/0161684 A1 * | 7/2008 | Li | A61B 5/06 600/426 |
| 2008/0255548 A1 | 10/2008 | Van Hal et al. | |
| 2009/0024023 A1 | 1/2009 | Welches et al. | |
| 2009/0131782 A1 | 5/2009 | Moonen et al. | |
| 2009/0131921 A1 * | 5/2009 | Kurtz | A61F 9/009 606/4 |
| 2009/0137988 A1 * | 5/2009 | Kurtz | A61F 9/00825 606/4 |
| 2009/0187176 A1 | 7/2009 | Assa et al. | |
| 2009/0198309 A1 | 8/2009 | Gowda et al. | |
| 2009/0275929 A1 * | 11/2009 | Zickler | A61F 9/00804 606/5 |
| 2009/0306498 A1 | 12/2009 | Bodduluri et al. | |
| 2010/0121142 A1 | 5/2010 | OuYang et al. | |
| 2010/0249570 A1 * | 9/2010 | Carson | A61B 5/0095 600/407 |
| 2010/0312136 A1 | 12/2010 | Cozzie | |
| 2010/0316734 A1 | 12/2010 | Hart et al. | |
| 2011/0082448 A1 | 4/2011 | Bruno-Raimondi | |
| 2011/0082451 A1 | 4/2011 | Melsky | |
| 2011/0152666 A1 | 6/2011 | Shanbhag et al. | |
| 2011/0218597 A1 | 9/2011 | Wang | |
| 2012/0022510 A1 * | 1/2012 | Welches | A61B 18/22 606/3 |
| 2012/0235909 A1 * | 9/2012 | Birkenbach | G06F 3/03542 345/158 |
| 2012/0253222 A1 | 10/2012 | Welches et al. | |
| 2013/0006093 A1 * | 1/2013 | Raleigh | A61B 6/584 600/411 |
| 2013/0023773 A1 | 1/2013 | Krishna et al. | |
| 2013/0102894 A1 | 4/2013 | Birngruber et al. | |
| 2013/0237973 A1 | 9/2013 | Kim et al. | |
| 2013/0303880 A1 | 11/2013 | Hsu | |
| 2013/0345685 A1 | 12/2013 | Poran et al. | |
| 2014/0074078 A1 | 3/2014 | Kumar et al. | |
| 2014/0088418 A1 | 3/2014 | Radulescu et al. | |
| 2015/0018725 A1 | 1/2015 | Sommer | |
| 2015/0057485 A1 * | 2/2015 | Carey | A61B 90/39 600/1 |
| 2015/0161802 A1 * | 6/2015 | Christiansen | A61B 90/94 348/74 |
| 2015/0327765 A1 * | 11/2015 | Crane | A61B 5/7435 348/77 |
| 2015/0335385 A1 * | 11/2015 | Miao | A61B 5/015 606/12 |
| 2019/0000564 A1 * | 1/2019 | Navab | G06T 7/521 |
| 2020/0000521 A1 * | 1/2020 | Miao | A61B 18/203 |

OTHER PUBLICATIONS

Kneebone, W.J., Thermal Imaging Guided Laser Therapy—Part 2, An Innovative Method for Determining Optimal Treatment Location and Effectiveness, Practical Pain Management, 2009.

(56) References Cited

OTHER PUBLICATIONS

Matthew S. Overley, Inftared Imaging: Critical Tools for Critical Times, Part 2: Infrared Imaging: Focus on Features, facilitiesnet.com, Mar. 2009.
Extended European Search Report of International Application No. 20208780.5 dated Feb. 11, 2021.

\* cited by examiner

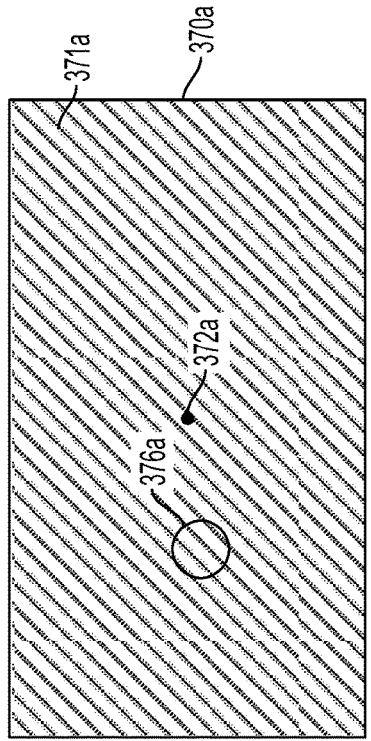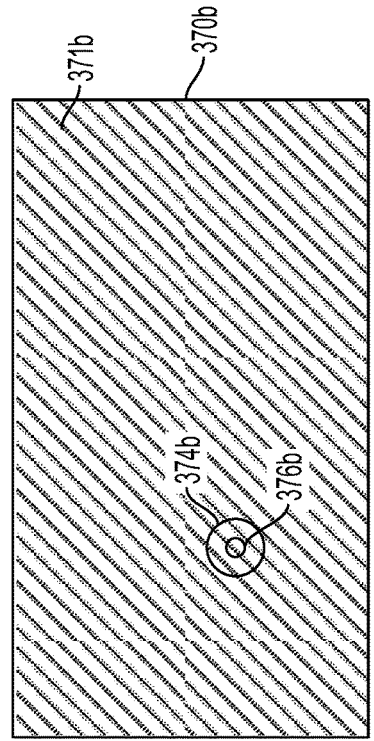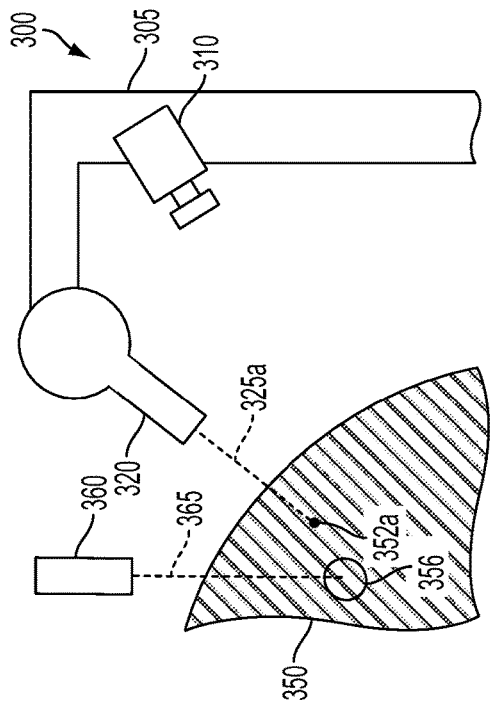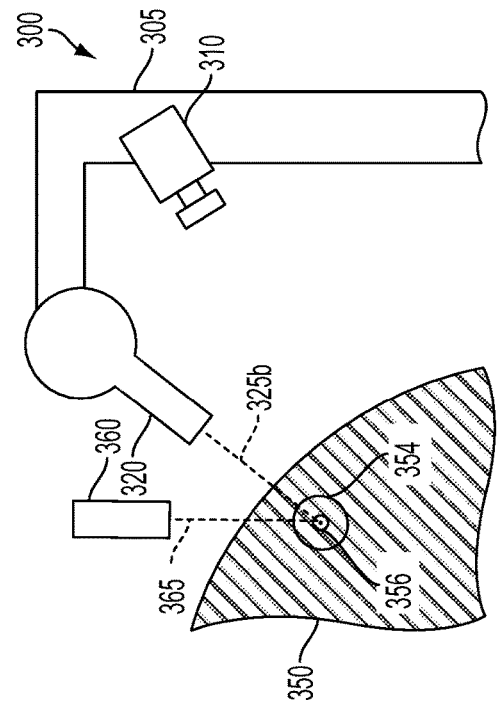

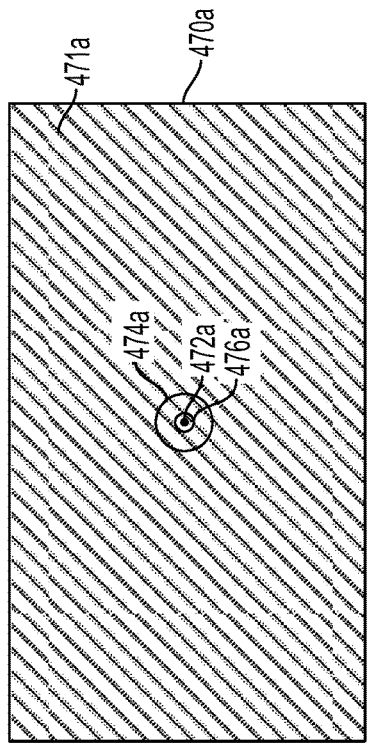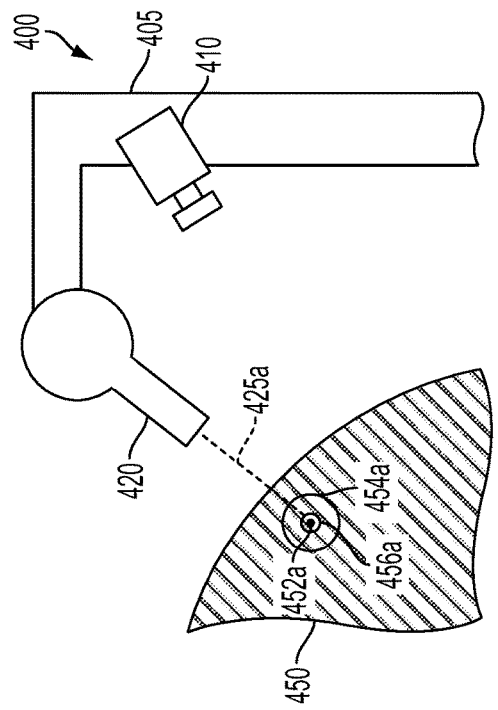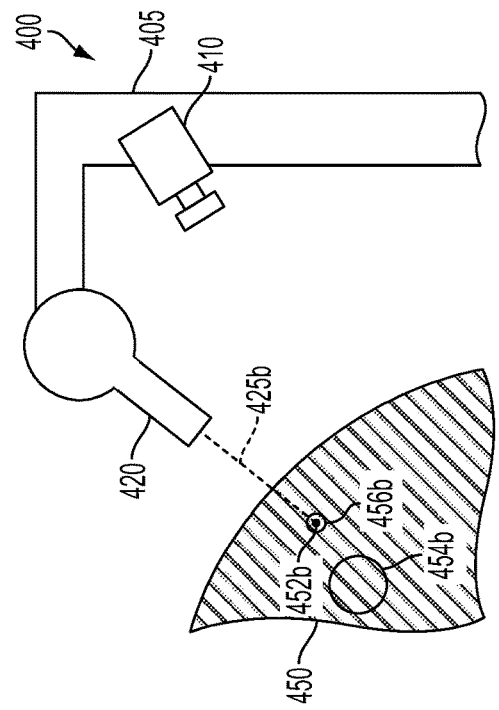
FIG. 4A
FIG. 4B
FIG. 4C
FIG. 4D

SYSTEM FOR LASER ABLATION SURGERY

CROSS-REFERENCE TO RELATED APPLICATION

This application is a continuation of and claims priority under 35 USC § 120 to U.S. patent application Ser. No. 14/282,989, filed on May 20, 2014, entitled "System for laser ablation surgery", which issued as U.S. Pat. No. 10,420,608, the entire contents of which are hereby incorporated by reference.

BACKGROUND

Unless otherwise indicated herein, the materials described in this section are not prior art to the claims in this application and are not admitted to be prior art by inclusion in this section.

A number of scientific methods have been developed to destroy, damage, excise, ablate, or otherwise alter biological tissues (e.g., malignant cancerous tumors). The methods include the use of sharpened surgical implements to remove the tissues by cutting, heated surgical implements to remove, ablate, or otherwise damage the tissues by the application of high temperatures, and the application of electrical and/or electromagnetic energies (e.g., RF energy, laser light) directly or indirectly to the tissues to induce changes in the tissues through the application of heat and/or electrical fields, or through other methods.

In some examples, $CO_2$, excimer, Nd:YAG, or other types of lasers are used to direct a high-energy beam of electromagnetic radiation at a tissue to be ablated. The high-energy beam of electromagnetic radiation acts to locally heat the tissue, ablating the tissue. Further, the high-energy beam can be very narrow, enabling the ablation of very small, precisely targeted tissues.

SUMMARY

Some embodiments of the present disclosure provide a system including: (i) an imager, wherein the imager is configured to image a biological tissue, wherein imaging the biological tissue comprises detecting infrared light received from the biological tissue, and wherein the infrared light received from the biological tissue is related to a temperature of the biological tissue; (ii) a heating laser, wherein the heating laser is configured to emit a beam of electromagnetic radiation at the biological tissue, wherein the beam of electromagnetic radiation causes localized heating of a target region of the biological tissue proximate to where the beam of electromagnetic radiation intersects with the biological tissue, and wherein the heating laser is configured to control the orientation of the emitted beam of electromagnetic radiation relative to the biological tissue; and (iii) a controller, wherein the controller is operatively coupled to the imager and the heating laser, and wherein the controller is configured to: (a) operate the imager to image the biological tissue; (b) determine a location of a high-temperature region of the biological tissue relative to the heating laser; and (c) operate the heating laser to control the orientation of the emitted beam of electromagnetic radiation such that the beam of electromagnetic radiation intersects with the biological tissue at a controlled location based on the determined location of the high-temperature region of the biological tissue.

Some embodiments of the present disclosure provide a method including: (i) operating an imager to image a biological tissue, wherein imaging the biological tissue comprises detecting infrared light received from the biological tissue, and wherein the infrared light received from the biological tissue is related to a temperature of the biological tissue; (ii) determining a location of a high-temperature region of the biological tissue relative to a heating laser, wherein the heating laser is configured to emit a beam of electromagnetic radiation at the biological tissue, wherein the beam of electromagnetic radiation causes localized heating of a target region of the biological tissue proximate to where the beam of electromagnetic radiation intersects with the biological tissue, and wherein the heating laser is configured to control the orientation of the emitted beam of electromagnetic radiation relative to the biological tissue; and (iii) operating the heating laser to control the orientation of the emitted beam of electromagnetic radiation such that the beam of electromagnetic radiation intersects with the biological tissue at a controlled location based on the determined location of the high-temperature region of the biological tissue.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3A illustrates an example active tracking system, an example specifying system, and an example target tissue.

FIG. 3B is an example image generated by an imager of the example active tracking system illustrated in FIG. 3A FIG. 3C illustrates the example active tracking system, the example specifying system, and the example target tissue illustrated in FIG. 3A after the example active tracking system has been operated relative to the example specifying system.

FIG. 3D is an example image generated by an imager of the example active tracking system illustrated in FIG. 3C FIG. 4A illustrates an example active tracking system and an example target tissue.

FIG. 4B is an example image generated by an imager of the example active tracking system illustrated in FIG. 4A FIG. 4C illustrates the example active tracking system and the example target tissue illustrated in FIG. 4A after the example target tissue has shifted.

FIG. 4D is an example image of generated by an imager of the example active tracking system illustrated in FIG. 4C

DETAILED DESCRIPTION

Figure 1:
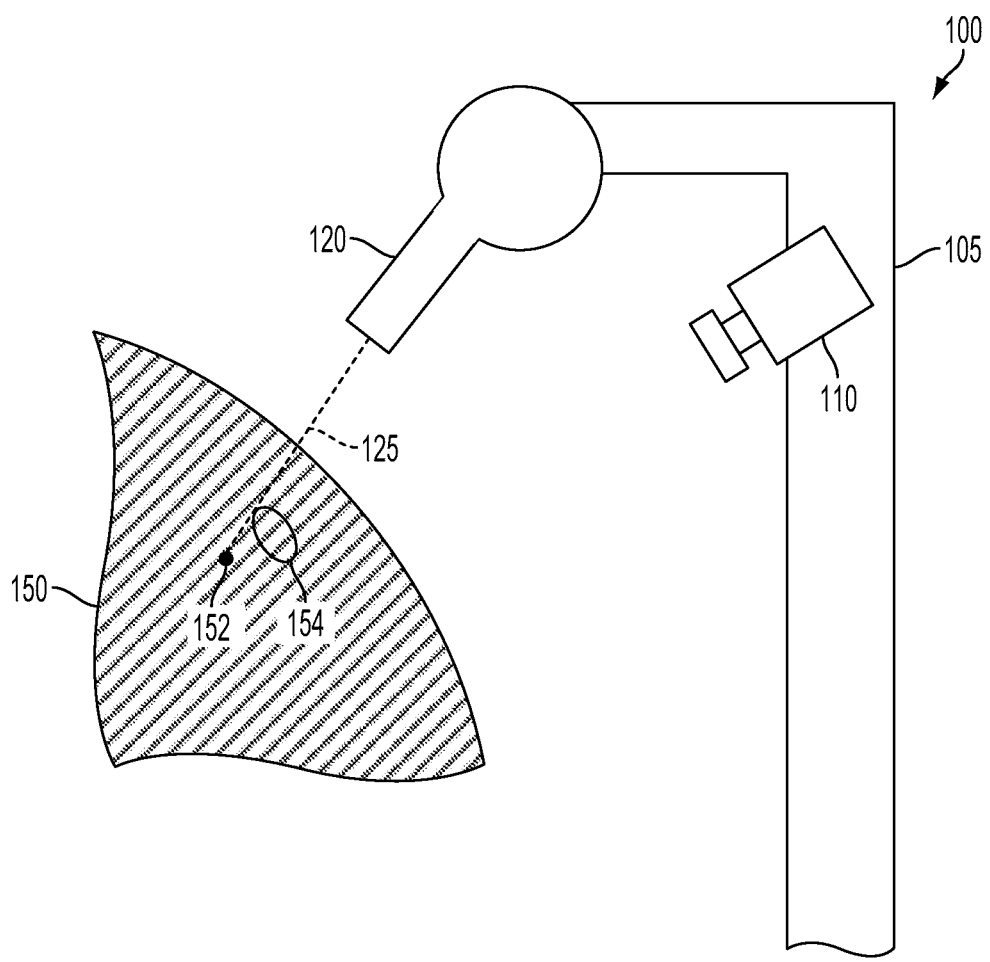
FIG. 1 illustrates an example active tracking system.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body and/or tissues thereof, it is contemplated that the disclosed methods, systems and devices may be used in any environment where active tracking of tissue or other object or element of an environment is desired. The environment may be any living or non-living body or a portion thereof, a work piece, an implantable device, etc. For example, one of skill in the art will recognize that the embodiments disclosed herein may be used to thermally 'tag' and track regions of a work piece moving along an assembly line or moving in some other industrial or fabrication process. Moreover, while the present disclosure describes embodiments for use in vivo, one of skill in the art will also recognize that in vitro applications are possible as well. Accordingly, the environment may also include a test tube or other vessel for holding a fluid, a transplant tissue, and/or a stereotaxically or otherwise immobilized tissue.

I. Overview

Lasers can be used to cause localized heating of an object or environment. In some examples, a surgical laser could be configured to direct a beam of electromagnetic radiation at a specified location on tissue of a human, and the beam of electromagnetic radiation could cause an increase in the temperature of the tissue proximate to the specified location. This localized heating could result in a variety of changes in the tissue (e.g., an increase in blood flow, denaturation and/or coagulation of proteins of the tissue, the destruction and/or ablation of the tissue) according to a variety of applications (e.g., destruction of cancerous tissue, reduction of varicose veins). In some examples, a laser could be used to melt, inscribe, drill a hole through, cut or otherwise modify a work piece (e.g., a sheet of metal) by causing an increase in the temperature of the work piece at a specified location. In some examples, the target of a laser could be mobile, compliant, or otherwise change position while the laser is being applied to heat the target. For example, the target could be a tissue of a body during a surgical procedure, and the biological activities of the body and/or the actions of a surgeon could cause the tissue to move or shift. After the movement or shift, the laser could be heating a tissue other than the target tissue.

An active tracking system includes an imager configured to image the environment containing the target of a heating laser, and to detect infrared light radiated from the environment such that the target can be tracked. That is, a target that is being heated by the heating laser could appear as a high-temperature region of the environment, as imaged by the imager, and the location of the target relative to the imager and/or heating laser could be determined based on a determined location of the high-temperature region. The heating laser could then be controlled such that the orientation of the beam of electromagnetic radiation is oriented toward the high-temperature region for continued heating of the target. The heated target region of the environment could be considered to be 'dynamically tagged' by the heating laser; that is, being heated by the heating laser allows the location of the target to be determined, using the imager, for a period of time after the heating laser ceases to emit the beam of electromagnetic radiation and/or the beam of electromagnetic radiation ceases to be oriented toward the target region.

The imager could include an infrared camera, one or more bolometers and/or pyrometers, actuated mirrors or other optics, or other elements. For example, the imager could be an infrared camera configured to detect infrared radiation having a wavelength between 9 and 14 micrometers. The imager could include more than one infrared or other variety of camera. The heating laser could include a variety of lasers having a variety of wavelengths according to a variety of applications. For example, the heating laser could be a surgical $CO_2$, excimer, Nd:YAG, or other type of laser. Further, the orientation of the beam of electromagnetic radiation emitted by the heating laser could be controlled through a variety of methods. For example, the body of the heating laser could be mounted on a gimbal or other mechanical armature, and the orientation (i.e., location and/or angular direction) of the heating laser could be controlled by servos, motors, galvanometers, or other mechanical actuators. Additionally or alternatively, optics of or relating to the heating laser could be controlled. For example, a set of mirrors mounted on galvanometers or otherwise mechanically actuated could reflect the beam of electromagnetic radiation emitted by the heating laser in a controlled direction toward a target region or other element of an environment.

Further, the imager could be substantially on an axis of the beam emitted by the laser, or the imager could be off-axis. The imager could include filters configured to substantially block electromagnetic radiation of wavelengths similar to wavelength of the beam of electromagnetic radiation emitted by the heating laser. Further, the imager could be configured to change orientation (e.g., could include actuators configured to control the location and/or angular direction of the imager). In some examples, this could include the imager being disposed on or proximate to the heating laser. In some examples, this could include the imager and heating laser including and/or being disposed relative to common optical elements such that the imager images a region along an orientation substantially similar to the orientation of the beam of electromagnetic radiation emitted by the heating laser.

The active tracking system could include a second laser configured to emit a second beam of electromagnetic radiation in substantially the same direction and along substantially the same axis (i.e., having substantially the same orientation) as the beam emitted by the heating laser. The imager, or a second imager, could be configured to detect light radiated from the environment due to the second beam of electromagnetic radiation emitted by the second laser. The orientation of the second beam of radiation could be controlled such that the detected location of the intersection of the second beam of radiation matched the detected location of the high-temperature region such that the beam of electromagnetic radiation emitted by the heating laser was oriented toward the high-temperature region.

Other methods and modes of operation of such an active tracking system are possible. For example, the active tracking system could be operated to heat a sequence of target regions in the environment. Additionally or alternatively, the imager could be calibrated or otherwise configured to detect the temperature of regions of the environment, and the magnitude of the output of the heating laser could be controlled relative to the detected temperature of a target region such that the temperature of the target region was substantially equal to a specified temperature, or to a series of specified temperatures at a respective series of points in time. In some embodiments, the active tracking system could initially operate the heating laser to heat a specified target region, and to 'tag' the specified target region by increasing the temperature of the target region. The active tracking system could subsequently operate such that the beam of electromagnetic radiation emitted by the heating laser continued to be oriented toward the tagged target region. The specified target region could be based on data from an imaging modality and/or could be specified manually, e.g., by a surgeon.

Other configurations, modes and methods of operation, and other embodiments are anticipated. The active tracking system could include another imager and/or another imaging modality to improve the control of the heating laser based according to an application. The heating laser and/or imager could be used to generate data about elements of the environment; for example, the heating laser and imager could be operated to generate a specific heat map of the environment by, e.g., measuring the rate at which different regions of the environment cool following the application of a specified amount of heat energy to the respective regions by the heating laser. An active tracking system could include multiple imagers, multiple lasers, and/or additional components according to an application. The active tracking system could be applied toward implementing a surgical intervention (e.g., ablation of a tissue), an industrial process (e.g., cutting a work piece), or some other application. In some examples, the active tracking system could be used only to dynamically track elements of an environment as the elements of the environment move or shift. Other applications and configurations of an active tracking system as described herein are anticipated.

It should be understood that the above embodiments, and other embodiments described herein, are provided for explanatory purposes, and are not intended to be limiting.

Further, the term "surgical intervention" as used herein should be understood broadly to include any activities applied toward the intentional modification of the anatomy of a human or animal body by the application of external forces and/or energies to the human or animal body; e.g., incisions, ablation by RF or other directed energies, excision, suturing, application of surgical adhesives, stapling, transplanting, cauterizing, sawing, abrading, applying a surgical fluid to (e.g., sterile, isotonic saline), cooling, heating, or any other surgical operation.

II. Example Active Tracking Systems

FIG. 1 illustrates an example active tracking system 100 and an example biological tissue 150. The active tracking system 100 includes an imager 110 and a heating laser 120 that can be operated to heat regions of the biological tissue 150. The imager 110 and heating laser 120 are disposed on a mount 105. The heating laser 120 can emit a beam of electromagnetic radiation 125 that intersects with the biological tissue at a target region 152. The beam of electromagnetic radiation 125 can cause heating of the target region 152. The location relative to the heating laser 120 of a high-temperature region 154 of the biological tissue 150 could be determined using the imager 110. The active tracking system 100 additionally includes a controller (not shown) configured to operate the heating laser 120 and imager 110 to enable functions and applications of the active tracking system 100 described herein.

The biological tissue 150 could be any tissue of a human or animal. The biological tissue 150 could have a number of properties relating to receiving electromagnetic energy (e.g., 125) and being heated by the electromagnetic energy. The biological tissue 150 could have an absorption spectrum that described the degree to which the biological tissue 150 absorbed and/or is heated by received electromagnetic radiation of various frequencies. For example, the absorption spectrum could be related to the presence of water, melanin, hemoglobin, or other substances in the tissue. A property of the beam of electromagnetic radiation 125 and/or the heating laser 120 (e.g., an emission wavelength) could be specified relative to properties of the biological tissue 150 (e.g., to maximize an efficiency of transduction of energy from the beam of electromagnetic radiation 125 into heat in the target region 152 of the biological tissue 150). The biological tissue 150 could have a specific heat relating a degree of temperature change of the tissue to an amount of heat energy gained/lost by the tissue. The biological tissue 150 could have a thermal conductivity relating to the rate at which heat is spatially transmitted within the biological tissue 150. Properties of the biological tissue 150 (e.g., absorption spectrum, specific heat, thermal conductivity) could be related to a medical state of the biological tissue 150. For example, a cancerous tissue could have a different thermal conductivity than a non-cancerous tissue.

The biological tissue 150 could be rigid or compliant. The biological tissue 150 could be an external tissue (e.g., skin, cornea, mucosa) or an internal tissue. In embodiments wherein the biological tissue 150 is an internal tissue, the biological tissue 150 could be exposed by surgical techniques including the creation of incisions in overlying tissue (e.g., using a scalpel or cutting laser to incise tissue, e.g., skin, that covers or otherwise occludes the biological tissue 150), applying retractors or other implements to displace overlying tissue, disposing elements of the active tracking system 100 in an internal volume proximate to the biological tissue 150 (e.g., disposing elements of the active tracking system 100 on an endoscopic instrument and operating the endoscopic instrument to inflate a volume neighboring the biological tissue 150 and to dispose the elements of the active tracking system 100 in the inflated volume), or other methods. The biological tissue 150 could be deformed and/or displaced in space by activity of the biological tissue 150, activity of neighboring tissues, movement of a body that includes the biological tissue 150, actions of a surgeon or other medical professional, forces applied by surgical instruments, or due to some other action or phenomenon. For example, the biological tissue 150 could be tissue of the chest wall of a person, and the tissue could have been exposed by making an incision into and retracting skin covering the chest wall. The biological tissue 150 could be moved by breathing motions of the person. Other biological tissues, movements of biological tissues, and methods of accessing biological tissues and/or disposing elements of an active tracking system proximate to biological tissue are anticipated.

In the example of FIG. 1, the biological tissue 150 includes a high-temperature region 154. The high-temperature region 154 has a temperature detectably different from the temperature of neighboring regions of the biological tissue 150. That is, the high-temperature region 154 can emit infrared light such that an image of the biological tissue 150 generated using the imager 110 could be used to detect the presence, location, and/or some other property of the high-temperature region 154 of the biological tissue. For example, the high-temperature region 154 could emit a detectably higher amount of infrared light than neighboring regions of the biological tissue 150. The high-temperature region 154 could be created by heating a localized region of the biological tissue 150, e.g., by operating the active tracking system 100 such that the beam of electromagnetic radiation 125 intersects with the biological tissue 150 proximate to the localized region. Additionally or alternatively, some other means could be used to heat the localized region of the biological tissue 150. For example, a second laser could be operated to emit a beam of electromagnetic energy toward the localized region of the biological tissue 150. In another example, a heating surgical instrument (e.g., a cauterizing tool) could be used to heat the localized region of the biological tissue 150.

The imager 110 could be any device capable of detecting infrared light received from the biological tissue 150 or from some other environment of interest. The imager 110 could include a variety of components, including infrared sensors, infrared cameras (e.g., a camera configured to image light having a wavelength between approximately 9 micrometers and approximately 14 micrometers), bolometers, microbolometers, focal plane arrays, or other devices and/or arrangements of devices configured to generate an image of a biological tissue 150 by detecting infrared light received from the biological tissue 150. The imager 110 could be actively cooled (e.g., could include a Sterling cycle refrigerator, could be exposed to a source of liquid nitrogen). The imager 110 could be configured and/or operated to determine the temperature of a region of the biological tissue 150 (e.g., a temperature of the high-temperature region 154) or of a region of some other environment of interest. The imager 110 could include an array of discrete infrared detectors or could include an integrated circuit that includes an array of infrared detectors patterned on the integrated circuit. The imager 110 could include infrared detectors that include InSb, InGaAs, HgCdTs, InAs, lead sulfide, lead selenide, vanadium oxide, lead zirconate titanate, lanthanum doped lead zirconate titanate, lead titanate, lead zinc niobate, lead strontium titanate, barium strontium titanate, barium titanate, Sb SI, or some other material that is sensitive to infrared light. The imager 110 could include a quantum-well photodetector.

The imager 110 could include one or more optical elements including but not limited to lenses, apertures, visible-light mirrors, infrared-light mirrors, diffraction gratings, filters (e.g., a filter configured to substantially block visible light while transmitting infrared light), or other optical elements configured to interact with infrared light received from the biological tissue 150 so as to enable imaging of the received infrared light. For example, the imager 110 could include an array of infrared-sensitive photodetectors and an aperture and lens configured to refract infrared light received from the biological tissue 150 such that the received infrared light is projected in-focus onto the array of infrared-sensitive photodetectors.

The imager 110 could additionally be configured to image other objects and/or to detect energy other than infrared light. In some examples, the imager 110 could be configured to detect visible light received from the biological tissue 150. For example, the imager 110 could include an array including infrared-sensitive photodetectors and visible-light-sensitive photodetectors. The imager could further include an aperture, a lens, and/or other optical elements configured to refract or otherwise modify infrared and visible light received from the biological tissue 150 such that the received light is projected in-focus onto the array of infrared-sensitive photodetectors and visible-light-sensitive photodetectors. Additionally or alternatively, the imager 110 could include an infrared camera and a visible light camera or some other combination of infrared imaging components and other energy sensitive components. For example, the imager 110 could include an infrared camera, a visible-light camera, and optics configured to split, filter, refract, or otherwise modify visible and infrared light received from the biological tissue 150 (or other imaged environment) such that the infrared camera and visible light camera can image substantially the same area of the biological tissue 150 at the same time. Additional or alternative detectors could be included in the imager to enable additional or alternative imaging modalities (e.g., visible light imaging, ultraviolet imaging, ultrasound imaging). The imager 110 could include a source of illumination (e.g., a visible light source, an infrared light source).

The imager 110 could be configured to rotate, translate, or otherwise move such that the region imaged by the imager 110 (i.e., a region in the direction of an optical axis of the imager 110) could be controlled and/or changed. For example, the imager 110 could be mounted on a gimbal. Movement of the imager 110 could be effected by servos, galvanometers, motors, or some other mechanical actuator(s). In some examples, motions of the imager 110 could be controlled to automatically track the biological tissue 150. In some examples, the imager 110 could be manually moved such that an optical axis of the imager 110 intersected with the biological tissue 150 (e.g., such that the imager 110 could image a region that includes the biological tissue 150). For example, the imager 110 could be positioned at the beginning of a surgical intervention to image the biological tissue 150.

The heating laser 120 could be any device configured to emit a directed beam of electromagnetic radiation 120 sufficient to cause localized heating of a target region 152 of the biological environment 150 (or some other environment of interest) proximate to where the emitted beam intersects with the biological environment 150 (or other environment of interest). The heating laser 120 could be a medical laser. The heating laser 120 could include a $CO_2$ laser, a semiconductor diode laser, a dye laser, an excimer laser, a fiber laser, a gas laser, a free electron laser, or some other type or types of laser. The heating laser 120 could include optical elements configured to affect one or more properties of the beam of electromagnetic energy emitted by the heating laser 120, e.g., lenses, mirrors, diffraction gratings, volume holographic gratings, collimators, nonlinear optical elements (e.g., frequency doubling or tripling media), or other elements. For example, the heating laser 120 could include a collimator configured to cause the beam of electromagnetic energy 125 to have a specified width.

The heating laser 120 could be configured such that one or more properties of the beam of electromagnetic energy 125 have a specified value. For example, the heating laser 120 could be configured such that a wavelength of the beam of electromagnetic energy 125 is a specified wavelength. The specified wavelength could be specified according to an application. For example, the specified wavelength could be an absorption wavelength of hemoglobin such that the beam of electromagnetic energy 125 preferentially heats blood. In another example, the specified wavelength could be an absorption wavelength of a contrast agent that is configured to bind to cancer cells such that the beam of electromagnetic energy 125 preferentially heats cancer cells and/or tumors. Additionally or alternatively, the specified wavelength could be a wavelength that is not substantially absorbed by a tissue to be spared during a surgical intervention. Other specified wavelengths and/or specified other properties of the beam of electromagnetic energy 125 are anticipated.

The heating laser 120 could be configured such that the orientation (i.e., the location and/or the angular direction) of the emitted beam of electromagnetic energy 125 is controllable. In some examples, this could include rotating, translating, or otherwise moving the heating laser 120. For example, the heating laser 120 could include a gimbal, a galvanometer, a motor, and/or some other actuators or other elements configured to change the location and/or orientation of the heating laser 120. Additionally or alternatively, the heating laser 120 could include optical elements actuated to control the orientation of the emitted beam of electromagnetic energy 125. For example, one or more mirrors could be mounted to galvanometers such that the mirrors reflect the beam of electromagnetic energy 125 and such that actuation of the galvanometers to rotate the mirrors causes a change in the direction of the beam of electromagnetic energy 125. For example, an output coupler or other electromagnetic energy source of the heating laser 120 could be coupled to a flexible optical fiber such that the beam of electromagnetic energy 125 is emitted from an end of the flexible fiber in a direction substantially parallel to the orientation of the end of the flexible fiber. The orientation of the end of the flexible fiber could be controlled by servos or other actuators to control the orientation of the emitted beam of electromagnetic energy 125. Other configurations and methods of controlling the orientation of the emitted beam of electromagnetic energy 125 are anticipated.

Note that the mount 105 is intended as a non-limiting example. Other means could be employed to secure the imager 110, heating laser 120, and other components of the active tracking system 100 in place relative to the biological tissue 150. For example, the imager 110, heating laser 120, and/or other components could be mounted on a surgical table, a wall, a ceiling, a cart, a wearable device worn by a surgeon or other person, a surgical device or implement (e.g., to the end of a laparoscopic and/or endoscopic instrument), or to some other support. The imager 110, heating laser 120, and/or other components could be part of some other surgical or other apparatus (e.g., an imaging system, a stereotactic surgical system, a robotic surgical system) and could be mounted to a mount, support, or other component(s) of the other surgical or other apparatus. Further, the active tracking system 100 could include additional components, e.g., fluorescent imagers, robotic surgical systems, CT and/or Xray imagers, MR imagers, ultrasonic imagers, laparoscopic and/or endoscopic systems, and/or other components according to an application. For example, the active tracking system 100 could include multiple imagers 110 and/or heating lasers 120.

As shown in FIG. 1, the imager 110 is not co-axial with the heating laser 120. That is, the heating laser 120 is not located on or substantially proximate to an optical axis of the imager 110 (e.g., an axis passing through the imager 110 and directed toward the center of a field of view of the imager 110); conversely, the imager 110 is not located on or substantial proximate to an emitted beam axis of the heating laser 120 (i.e., an axis substantially coincident with the beam of electromagnetic energy 125). In some embodiments, the imager 110 and heating laser 120 could be co-axial; that is, the imager 110 and heating laser 120 could be disposed proximate to each other such that the emitted beam of electromagnetic radiation 125 originated from a point substantially the same as an optical feature (e.g., an aperture) of the imager 110. For example, the imager 110 could be disposed on the heating laser 120 such that movements of the heating laser 120 to orient the beam of electromagnetic radiation 125 additionally orient an optical axis and/or location of the imager 110. In some examples, the imager 110 could include a filter configured to block light having wavelengths corresponding to a wavelength of the beam of electromagnetic radiation 125 emitted by the heating laser 120. For example, the heating laser 120 could be an excimer laser configured to emit a beam of electromagnetic radiation 125 having a wavelength of approximately 150 nanometers and the imager 110 could be an infrared imager configured to detect infrared light and to include a filter configured to substantially block light having a wavelength of approximately 150 nanometers such that the imager 110 detected substantially no light emitted by the heating laser 120 (e.g., light emitted by the heating laser 120 that is reflected specularly off of the biological tissue 150 toward the imager 110). In some examples, the imager 110 and heating laser 120 could include and/or be disposed relative to common optical elements such that the imager 110 images a region along an orientation substantially similar to the orientation of the beam of electromagnetic radiation 125 emitted by the heating laser 120.

In embodiments wherein the imager 110 and heating laser 120 are co-axial, control of the heating laser 120 relative to the location of the high-temperature region 154 determined by the imager 110 could be simplified, taking into account the imager 110 and heating laser 120 being co-axial. For example, a simple mapping between points in an image generated using the imager 110 and angles of the beam of electromagnetic radiation 125 emitted by the heating laser 125 could be determined and used to control the heating laser 120 such that the beam of electromagnetic radiation 125 is emitted in a direction such that the beam of electromagnetic radiation 125 interests with the biological tissue 125 at a controlled location that is based on a location of the high-temperature region 154 determined using the imager 110. Other methods of controlling the heating laser 120 based on information (e.g., images of the biological tissue 150) generated by the imager 110 and/or other information are anticipated.

The heating laser 120 could be operated such that the location of the target region 152 (i.e., the location at which the beam of electromagnetic radiation 125 intersect with the biological tissue 150) is maintained proximate to the high-temperature region 154. The heating laser 120 could be further operated to maintain the temperature of the high-temperature region 154 at a temperature greater than the temperature of regions of the biological tissue 150 that neighbor the high-temperature region. In some examples, the imager 110 could be configured to determine the temperature of the high-temperature region 154 and the power of the beam of electromagnetic radiation 125 could be controlled based on the detected temperature of the high-temperature region 154 to maintain the temperature of the high-temperature region 154 substantially equal to a specified temperature. For example, the specified temperature could be a temperature at which blood coagulates or at which some other biological process occurs. In some examples, the heating laser 120 could be operated to cause localized heating of a target region of the biological tissue 150 (or of a target region of some other environment of interest) sufficient to cause an irreversible change in elements of the target region of the biological tissue 150 (or other environment of interest). For example, the heating laser 120 could be operated to ablate, burn, melt, vaporize, coagulate, polymerize, denature, evaporate, sublimate, inscribe, or effect some other change in elements (e.g., fluids, proteins, polymers, crystals, particles) of a controlled region of the biological tissue 150 (or of some other environment of interest).

The active tracking system 100 could include additional elements or components (not shown). The active tracking system 100 could include one or more controllers configured to operate the imager 110, heating laser 120, and/or other elements of the active tracking system 100. The active tracking system 100 could include communications devices (wireless radios, wired interfaces) configured to transmit/receive information to/from other systems (e.g., servers, medical imaging devices, surgical implements, surgical robots) to enable functions and applications of the active tracking system 100. For example, the active tracking system 100 could include an interface configured to receive imaging information about the biological tissue 150. The active tracking system 100 could include an interface configured to present information about the active tracking system 100 to a user and/or to allow the user to operate the active tracking system. Additionally or alternatively, the active tracking system 100 could be configured to communicate with another system (e.g., a cellphone, a tablet, a computer, a remote server) and to present a user interface using the remote system. In some examples, the active tracking system 100 could be part of another system. For example, the active tracking system 100 could be implemented as part of a robotic surgical system (e.g., the imager 110, heating laser 120, and other component configured as described herein could be disposed as part of a robotic surgical system and could be operated as described herein). In some examples, the active tracking system 100 could include multiple imagers 110, multiple heating lasers 120, or other additional components. The active tracking system 100 could include sensors and/or be in communication with sensors configured to image other properties of the biological tissue 150 (or other environment of interest). For example, the active tracking system 100 could include a fluorescent imager configured to image the location of fluorescent markers disposed in the tissue that are configured to selectively bind with cancer cells. Other configurations, operations, and applications of active tracking systems as described herein are anticipated.

Figure 2A:
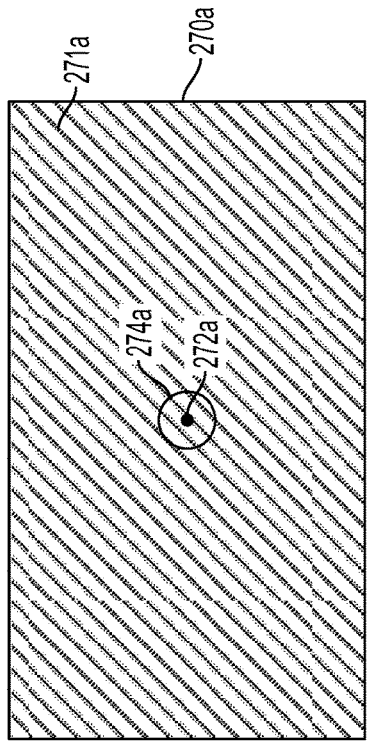
FIG. 2A illustrates an example active tracking system and an example target tissue.

FIG. 2A illustrates an example active tracking system 200 that includes an imager 210, a heating laser 220, and a mount. During a first period of time, a first beam of electromagnetic radiation 225a is oriented toward a biological tissue 250 such that the first beam of electromagnetic radiation 225a intersects with the biological tissue 250 at a first target region 252a. The first target region 252a is within a first high-temperature region 254a of the biological tissue 250.

Figure 2B:
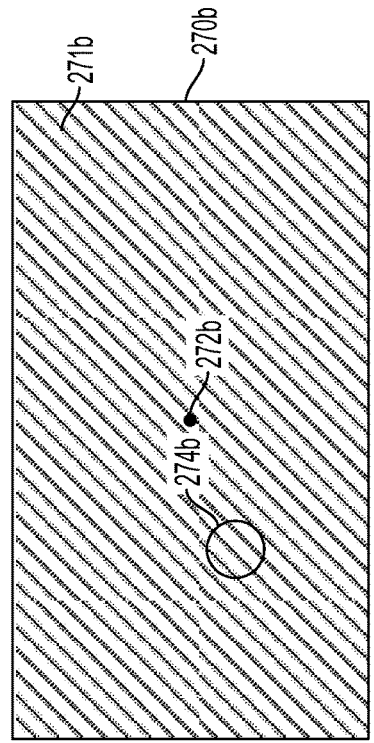
FIG. 2B is an example image generated by an imager of the example active tracking system illustrated in FIG. 2A

FIG. 2B illustrates a first example image 270a that could be generated using the imager 210 during the first period of time (i.e., the period of time illustrated in FIG. 2A). The first example image 270a includes a first image of the biological tissue 271a related to infrared light received from the biological tissue 250 during the first period of time by the imager 210. The first image of the biological tissue 271a includes an image of the first high-temperature region 274a. A first determined target region 272a represents the location on the first image of the biological tissue 271a corresponding to the first target region 252a. Note that the first determined target region 272a is not a feature of the first image of the biological tissue 271a; rather, the first determined target region 272a is determined based on the configuration (e.g., location, orientation) of the imager 210 and heating laser 220. During the first period of time, the first target region 252a is within with the first high-temperature region 254a; correspondingly, the first determined target region 272a is proximate to the image of the first high-temperature region 274a.

The location of the image of the first high-temperature region 274a (or of images of high temperature regions in images generated by the imager 210 in general) in the first image of the biological tissue 271a could be effected using a variety of methods. In some examples, a threshold operation could be applied to the received infrared light and circle-fitting or some other centroid-locating operation could be applied to the thresholded data to determine the location of an image of a high-temperature region of tissue within an image of a biological tissue or other environment of interest. Peak detection, wavelet decomposition, fitting of a Gaussian or other distribution, or some other algorithm or combination of algorithms could be employed to determine the presence and/or location of an image of a high-temperature region within an image of a biological tissue or other environment of interest. Further, the temperature or other information about the high-temperature region corresponding to the image of the high-temperature region could be determined; for example, the amplitude of the detected received infrared light corresponding to the high-temperature region could be used (e.g., using a look-up table or other method) to determine the temperature of the high-temperature region. Such methods could additionally or alternatively be used to determine the temperature or other information about other regions of an environment imaged by the imager 210.

The location of the first high-temperature region 254a and/or first target region 252a relative to elements of the active tracking system 200 (e.g., heating laser 220) and/or relative to elements of the first example image 270a (or any other image) generated by the imager 210 could be effected using a variety of methods. In some examples, a mapping or other model or algorithm could be used to relate a determined location of the image of the first high-temperature region 274a in the first example image 270a to the location of the corresponding first high-temperature region 274a. For example, an algorithm could determine that the first high-temperature region 274a is located proximate to the intersection between a ray extending from the imager 210 in a direction determined by the location of the image of the first high-temperature region 274a within the first example image 270a and a plane proximate to and coextensive with a surface of the biological tissue 250. In some examples, a mapping or other model or algorithm could be used to determine the location of the first target region 252a relative to elements of the active tracking system 200 and/or the location of the first high-temperature region 254a based on information about the orientation, location, or other information about the heating laser 220. For example, the heating laser 220 and the imager 210 could be co-axial, such that a mapping could be determined between the angle of the orientation of the heating laser 220 (e.g., the direction of the first beam of electromagnetic radiation 225a relative to elements of the active tracking system 200) and image locations in the first example image 270a (or any other image) generated by the imager 210. The determined mapping could be used to determine the location of the first target region 252a.

In some examples, one or more parameters of a mapping, algorithm, or other method for determining the location of the first high-temperature region 254a and/or first target region 252a relative to elements of the active tracking system 200 (e.g., heating laser 220) and/or relative to elements of the first example image 270a (or any other image) generated by the imager 210 could be determined through a calibration process. For example, the heating laser 220 could be operated to emit a beam of electromagnetic radiation having a specified orientation, and the location of a resulting high-temperature region of the biological tissue 250 and/or of a corresponding image of such a high temperature region within the field of view of the imager 210 could be determined. The determined location could be associated with the specified orientation of the heating laser 220. Other methods of calibrating the operation of the active tracking system 200 or otherwise determining information to operate the active tracking system 200 are anticipated.

In some examples, determining the location of the first high-temperature region 254a and/or first target region 252a relative to elements of the active tracking system 200 (e.g., heating laser 220) and/or relative to elements of the first example image 270a (or any other image) generated by the imager 210 could be related to information about the biological tissue 250 generated by some other imaging system or modality. For example, a CT scanner, ultrasound scanner, MR imager, or other device or combination of devices could be used to determine a location, size, geometry, or other information about the biological tissue 250 and the determined information could be used to determine the location of the first high-temperature region 254a and/or first target region 252a.

Note that, during the first time period (aspects of which are illustrated in FIGS. 2A and 2B), the first beam of electromagnetic radiation 255a is oriented in a direction such that the first target region 252a is within with the first high-temperature region 254a of the biological tissue 250. This situation could have come about as a result of a controller or some other system (e.g., a component of the active tracking system 200) operating the heating laser 220 (e.g., operating an orienting actuator to control the orientation of the heating laser 220 and a power controller to modulate the power output of the heating laser 220) such that the first beam of electromagnetic radiation 255a intersects with the biological tissue 250 at a controlled location (i.e., the first target region 252a) to heat the first high-temperature region 254a. In some examples, the controlled location could be based on a determined location of the first high-temperature region 254a (e.g., the imager 210 could be operated to image the biological tissue 250 (including imaging the first high-temperature region 254a) such that the location of the first high-temperature region 254a could be determined). For example, the controlled location could be specified to be substantially equal to the determined location of the first high-temperature region 254a. Additionally or alternatively, the controlled location could be specified relative to the determined location of the first high-temperature region 254a such that, over a number of subsequent time periods (e.g., subsequent to the first time period), the heating laser 220 could heat, ablate, burn, or otherwise effect a change in a series of target regions of the biological tissue 250. For example, the heating laser 220 could be operated to ablate tissue along a specified trajectory on the surface of the biological tissue 250.

In some examples, the heating laser 220 could be operated as described above to control the orientation of a beam of electromagnetic radiation emitted by the heating laser 220 such that the beam of electromagnetic radiation intersects with the biological tissue 250 proximate to the determined location of a high temperature region of the biological tissue 250 (e.g., first high-temperature region 254a). This could include adjusting the orientation of the beam of electromagnetic radiation emitted by the heating laser 220 a plurality of times per second (e.g., at a specified sampling and/or update rate) such that the beam of electromagnetic radiation intersects with the biological tissue 250 proximate to a determined location of a high temperature region of the biological tissue 250 (i.e., the location of the high temperature region could be determined a plurality of times per second). In some examples, the heating laser 220 could be operated to alter the orientation of the beam of electromagnetic radiation only when a determined distance between a determined location of the high temperature region of the biological tissue 250 and a determined location at which the beam of electromagnetic radiation intersects with the biological tissue 250 exceeds a threshold value. Other methods of operating the heating laser 220, the imager 210, and/or other elements of the active tracking system 200 to determine the location of a high-temperature region of the biological tissue 250 and to direct a beam of electromagnetic radiation emitted by the heating laser 220 toward the determined location of the high temperature region are anticipated.

Figure 2C:
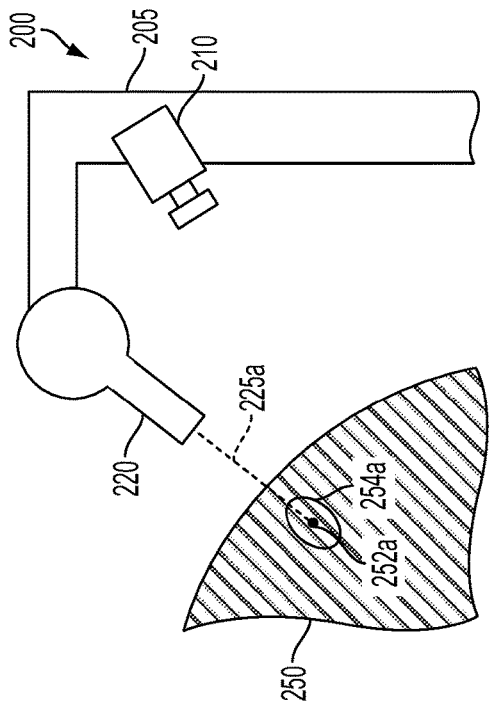
FIG. 2C illustrates the example active tracking system and the example target tissue illustrated in FIG. 2A after the example target tissue has shifted.

FIG. 2C illustrates the example active tracking system 200 of FIG. 2A during a second time period. The biological tissue 250 has shifted, deformed, or otherwise changed such that the region of the biological tissue 250 corresponding to the first high-temperature region 254a during the first time period corresponds to the second high-temperature region 254b during the second time period. A second beam of electromagnetic radiation 225b is directed toward the biological tissue 250 such that the second beam of electromagnetic radiation 225b intersects with the biological tissue 250 at a second target region 252b. The heating laser 220 is oriented in the same direction during the second time period as during the first; as such, the second target region 252b is not within with the second high-temperature region 254b of the biological tissue 250.

Figure 2D:
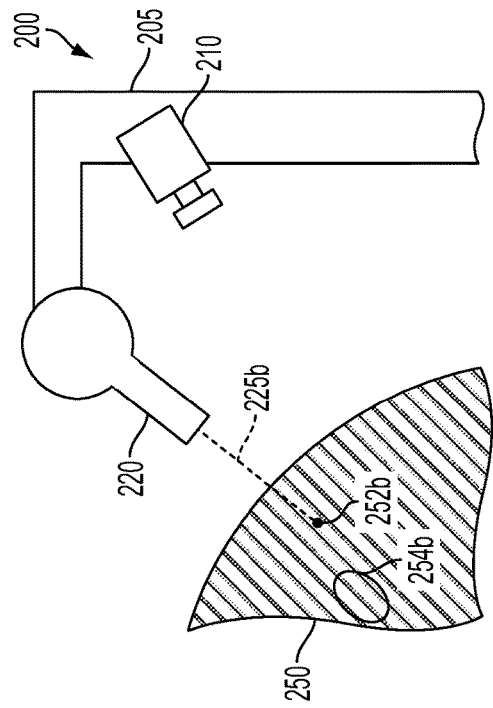
FIG. 2D is an example image generated by an imager of the example active tracking system illustrated in FIG. 2C

FIG. 2D illustrates a second example image 270b that could be generated using the imager 210 during the second period of time (i.e., the period of time illustrated in FIG. 2C). The second example image 270b includes a second image of the biological tissue 271b related to infrared light received from the biological tissue 250 during the second period of time by the imager 210. The second image of the biological tissue 271b includes an image of the second high-temperature region 274b. A second determined target region 272b represents the location on the second image of the biological tissue 271b corresponding to the second target region 252b. Note that the second determined target region 272b is not a feature of the second image of the biological tissue 271b; rather, the second determined target region 272b is determined based on the configuration (e.g., location, orientation) of the imager 210 and heating laser 220. During the second period of time, the second target region 252b is not collocated with the second high-temperature region 254b; correspondingly, the second determined target region 272b is separate from the image of the second high-temperature region 274b.

The heating laser 220 could be operated, based at least on information (e.g., images) generated by the imager 210, to change the orientation of the second beam of electromagnetic radiation 255b such that the second target region 254b is within with the second high-temperature region 254b and/or directed toward a desired location relative to the location of the second high-temperature region 254b. This could include determining the location of the second high-temperature region 254b and/or second target region 252b relative to elements of the active tracking system 200 (e.g., heating laser 220) and/or relative to elements of the second example image 270b (or any other image) generated by the imager 210. In some examples, this could include determining a set of commands (e.g., actuator operations, galvanometer angles, servomotor rotations) based at least on information in the second example image 270b sufficient to change the orientation of the heating laser 220 such that a beam of electromagnetic radiation emitted by the heating laser 220 intersects with the biological tissue 250 proximate to the second high-temperature region 254b. In some examples, this could include operating the heating laser 220 such that the orientation of a beam of electromagnetic radiation emitted by the heating laser 220 changes a small amount during respective time periods (e.g., update periods) of a plurality of time periods such that the location at which the beam of electromagnetic radiation emitted by the heating laser 220 intersects the biological tissue 250 changes incrementally to approach the second high-temperature region 254b. Other methods of operating the heating laser 220, imager 210, and other elements of the active tracking system 200 (e.g., to heat, burn, ablate, or otherwise affect a plurality of regions of the biological tissue 250 along a specified trajectory during a plurality of respective subsequent periods of time) are anticipated.

In general, the active tracking system 200 could be operated to track a specified region of the biological tissue 250 despite relative motion of the specified region relative to the active tracking system. This could be achieved by 'tagging' the specified region using heat delivered by the heating laser 220 and detected using the imager 210. In some examples, a power, pulse width, duration of application of heat, or some other property or properties of the beam of electromagnetic energy emitted by the heating laser 220 to effect the described functions could be specified to cause some reversible or irreversible change in the biological tissue 250 (or in some other environment of interest). For example, the active tracking system 200 could be operated to effect ablation, burning, vaporization, coagulation, denaturation, cauterization, or some other change elements of a specified region of the biological tissue 250 or of some other environment of interest. Operation of the heating laser 220 relative to information (e.g., images of infrared light received from the biological tissue 250 and related to the temperature of regions of the biological tissue 250) generated by the imager 210 could enable such changes to be effected in a specified target region of a biological tissue (or other environment of interest) despite deformation, translation, or other relative motion of the specified target region. In some examples, the heating laser 220 could be operated to cause a specified change in temperature of the specified target region such that the specified target region could be tracked using the imager 210 and/or heating laser 220 and such that substantially no irreversible changes are effected in the specified target region. Other applications and methods of operation of an active tracking system as described herein are anticipated.

In some examples, a location of the biological tissue 250 could be specified, and the heating laser 220 and/or other elements of the active tracking system 200 could be operated during an initial time period to direct a beam of electromagnetic radiation emitted by the heating laser 220 toward the specified location of the biological tissue 250. In some examples, the specified location could be specified based on information from an imaging device (e.g., CT scanner, MR imager, ultrasound scanner), the location of one or more anatomical landmarks of the biological tissue 250, one or more fiducials or other markers disposed on or in the biological tissue, or some other information. In some examples, the heating laser 220 could be operated to heat the specified location during the initial time period such that the specified location becomes a high-temperature region, and further, such that the imager 210 could be used to determine the location of the specified location during time periods subsequent to the initial time period.

III. Example Uses and Applications of an Active Tracking System

An active tracking system as described herein could be operated to provide a variety of functions and applications related to the tracking, ablating, heating, or otherwise altering and/or measuring through the application of heat specified regions of various environments of interest (e.g., a biological tissue of a human undergoing some surgical intervention).

In some examples, an active tracking system could be configured to track, ablate, or otherwise alter and/or measure multiple target regions within an environment of interest simultaneously. In some examples, this could include operating a plurality of heating lasers and/or a plurality of imagers as described herein to actively track, by application of heat using beams of electromagnetic energy emitted by the one or more heating lasers of the active tracking system, a respective plurality of target regions. In some examples, this could include using a single heating laser to heat multiple target regions by repeatedly changing the orientation of the beam of electromagnetic radiation emitted by the heating laser such that the beam is directed toward each of the target regions during respective periods of time.

In some examples, the imager and heating laser of an active tracking system could be operated to determine one or more thermal properties of a target region of an environment of interest. Thermal properties that the active tracking system could determine include but are not limited to specific heat, heat of vaporization, and thermal conductivity. In some examples, the active tracking system could be operated to determine one or more thermal properties of a plurality of points in an environment of interest. The active tracking system could be operated to determine one or more thermal properties of an environment of interest using a variety of methods. In some examples, the thermal conductivity and/or specific heat of a target region of an environment of interest could be determined by using an imager of the active tracking system to determine the temperature of the target region and/or regions neighboring the target region at one or more points in time relative to a period of time during which a specified amount of heat energy is delivered to the target region using the heating laser. For example, the active tracking system could be operated to generate a map of thermal conductivity of a biological tissue by applying a specified amount of heat energy to a plurality of specified regions of the biological tissue (e.g., regions having a regular spacing, as on a grid, on the surface of the biological tissue) at respective points in time and using the imager to determine the temperature across the biological tissue at respective points in time. The thermal conductivity of the plurality of specified regions could be determined based on a detected pattern of change of temperature across the biological tissue relative to the locations and points in time of the delivered specified amounts of energy. Other methods of operation and applications of active tracking systems as described herein to determine thermal properties of environments of interest (e.g., biological tissues) are anticipated.

In some examples, operation of an active tracking system (e.g., to ablate a specified region of a biological tissue) to heat or otherwise thermally affect an environment of interest could be related to and/or based on thermal properties of the environment of interest determined using the active tracking system. For example, the active tracking system could be operated to ablate, coagulate, or otherwise alter a target region by operating a heating laser relative to information generated by an imager such that the power of a beam of electromagnetic radiation emitted by the heating laser is modulated such that a temperature of the target region is substantially equal to a specified temperature (e.g., a temperature at which proteins of the target region can denature). Additionally or alternatively, the heating laser could be operated to apply heat energy to a target region until a detected thermal conductivity (e.g., detected using detected infrared light received from the target region using the imager) of the target region changed to a value indicating that the target region had been ablated. Other methods of operation of an active tracking system to effect specified change(s) in a target environment (e.g., a biological tissue) are anticipated.

In some examples, an active tracking system as described herein could be operated in combination with a targeting system, spotting system, or other type of target-region-indicating device or apparatus. FIG. 3A illustrates an example active tracking system 300 that includes an imager 310, a heating laser 320, and a mount 305 configured as described herein during a first period of time. A first beam of electromagnetic radiation 325a is directed toward a biological tissue 350 such that the first beam of electromagnetic radiation 325a intersects with the biological tissue 350 at a first target region 352a. Additionally, a spotting laser 360 is emitting a spotting beam of electromagnetic radiation 365 toward the biological tissue 350 such that the spotting beam of electromagnetic radiation 365 intersects with the biological tissue 350 at a spotted region 356. The imager 310 is additionally configured to image electromagnetic radiation emitted by the spotting laser 360.

FIG. 3B illustrates a first example image 370a that could be generated using the imager 310 during the first period of time (i.e., the period of time illustrated in FIG. 3A). The first example image 370a includes a first image of the biological tissue 371a related at least to infrared light received from the biological tissue 350 during the first period of time by the imager 310. The first image of the biological tissue 371a includes an image of the spotted region 376a due to light emitted by the spotting laser 360 and received by the imager 310 after reflecting, scattering, or otherwise interacting with the biological tissue 350. A first determined target region 372a represents the location on the first image of the biological tissue 371a corresponding to the first target region 352a. Note that the first determined target region 372a is not a feature of the first image of the biological tissue 371a; rather, the first determined target region 372a is determined based on the configuration (e.g., location, orientation) of the imager 310 and heating laser 320. During the first period of time, the first target region 352a is not within the spotted region 365; correspondingly, the first determined target region 372a is not proximate to the image of the spotted region 376a.

In some examples, the first time period of FIGS. 3A and 3B could be an initial time period. The location of the spotted region 365 could be specified using the spotting laser 360, and the heating laser 320 and/or other elements of the active tracking system 300 could be operated during a second time period (illustrated in FIG. 3C) to direct a second beam of electromagnetic radiation 325b using the heating laser 320 toward the spotted region 356. In some examples, the heating laser 320 could be operated to heat the spotted region 365 during the second time period such that the spotted region 365 becomes a high-temperature region 354, and further, such that the imager 310 could be used to determine the location of the spotted region 365/high-temperature region 354 during time periods subsequent to the initial time period.

FIG. 3D illustrates a second example image 370b that could be generated using the imager 310 during the second period of time (i.e., the period of time illustrated in FIG. 3C). The second example image 370b includes a second image of the biological tissue 371b related at least to infrared light received from the biological tissue 350 during the second period of time by the imager 310. The second image of the biological tissue 371b includes an image of the high-temperature region 374. The second image of the biological tissue 371b additionally includes an image of the spotted region 376b due to light emitted by the spotting laser 360 and received by the imager 310 after reflecting, scattering, or otherwise interacting with the biological tissue 350. During the second period of time, the high temperature region 354 coincides with the spotted region 356; correspondingly, the image of the high-temperature region 374 is proximate to the image of the spotted region 376b.

In some examples, the spotting laser 360 could be operated to indicate a specified location based on information from an imaging device (e.g., CT scanner, MR imager, ultrasound scanner), the location of one or more anatomical landmarks of the biological tissue 350, one or more fiducials or other markers disposed on or in the biological tissue, the judgments of a surgeon or other user, or some other information. The spotting laser 360 could be a handheld device, a device disposed on an articulated or otherwise actuated apparatus, a component of an imaging system, or configured in some other way. The spotting laser 360 could emit visible light, infrared light, ultraviolet light, or some other type of directed electromagnetic radiation. Conversely, the imager could be configured in a variety of ways to detect the light emitted by the spotting laser 360. In some examples, this could include the imager 310 comprising a camera having a first set of sensors configured to detect infrared light received from the biological tissue 350 and a second set of sensors configured to detected light emitted by the spotting laser 360 and reflected, scattered, or otherwise received from the biological tissue 350. In some examples, this could include the imager 350 comprising a first camera configured to detect infrared light received from the biological tissue 350 and a second camera configured to detected light emitted by the spotting laser 360 and reflected, scattered, or otherwise received from the biological tissue 350.

In some examples, the active tracking system could include a second laser disposed on the heating laser such that a second beam of electromagnetic radiation emitted by the second laser intersects with an environment of interest at a location proximate to a location at which a beam of electromagnetic radiation emitted by the heating laser intersects with the environment of interest. The second beam of electromagnetic radiation could be configured to illuminate a region of an environment of interest such that the illumination could be imaged (e.g., using an imager of the active tracking system) and such that the imaged illuminated region could be used to determine a target region of the environment being heated by the beam of electromagnetic radiation emitted by the heating laser. The use of a second laser configured as described above could allow for the operation of an active tracking system with less calibration and/or model information about the configuration of the active tracking system and/or an environment of interest. This could be achieved by operating the heating laser based on a detected location of the intersection of the beam of electromagnetic radiation emitted by the second laser relative to a detected location of a high-temperature region of the environment of interest. For example, the heating laser could be operated in a feedback mode such that the detected location of the intersection of the beam of electromagnetic radiation emitted by the second laser is moved toward the detected location of the high-temperature region of the environment of interest.

FIG. 4A illustrates an example active tracking system 400 that includes an imager 410, a heating laser 420, and a mount 405 configured as described herein during a first period of time. The heating laser 420 further includes a second laser configured to emit a second beam of electromagnetic radiation such that the second beam of electromagnetic radiation intersects with the biological tissue 450 at a location proximate to a location at which a beam of electromagnetic radiation emitted by the heating laser intersects with the biological tissue 450. The two beams of electromagnetic radiation (emitted by the heating laser and the second laser) comprise a first combined beam of electromagnetic radiation 425a that is directed toward a biological tissue 450 such that the first beam of combined electromagnetic radiation 425a intersects with the biological tissue 450 at a first target region 452a. The first target region 452a is within a first high-temperature region 454a of the biological tissue 450. Further, the first combined beam of electromagnetic radiation 425a results in a first illuminated spot 456a on the biological tissue 450. The second laser could be configured to emit ultraviolet, visible, infrared, or some other wavelength or wavelengths of directed electromagnetic radiation.

FIG. 4B illustrates a first example image 470a that could be generated using the imager 410 during the first period of time (i.e., the period of time illustrated in FIG. 4A). The first example image 470a includes a first image of the biological tissue 471a related at least to infrared light received from the biological tissue 450 during the first period of time by the imager 410. The first image of the biological tissue 471a includes an image of the first high-temperature region 474a. A first determined target region 472a represents the location on the first image of the biological tissue 471a corresponding to the first target region 452a. Note that the first determined target region 472a is not a feature of the first image of the biological tissue 471a; however, the first determined target region 472a could be determined based on the location of an image of the first illuminated spot 476a. During the first period of time, the first target region 452a is within the first high-temperature region 454a; correspondingly, the first determined target region 472a and the first illuminated spot 476a are proximate to the first high-temperature region 474a.

Note that, during the first time period (aspects of which are illustrated in FIGS. 4A and 4B), the first combined beam of electromagnetic radiation 455a is oriented in a direction such that the first target region 452a is within the first high-temperature region 454a of the biological tissue 450. This situation could have come about as a result of a controller or some other system (e.g., a component of the active tracking system 400) operating the heating laser 420 (e.g., operating an orienting actuator to control the orientation of the heating laser 420 and a power controller to modulate the power output of the heating laser 420) such that the first combined beam of electromagnetic radiation 455a intersects with the biological tissue 450 at a controlled location (i.e., the first target region 452a) to heat the first high-temperature region 454a. In some examples, the controlled location could be based on a determined location of the first high-temperature region 454a (e.g., the imager 410 could be operated to image the biological tissue 450 (including imaging the first high-temperature region 454a) such that the location of the first high-temperature region 454a could be determined). For example, the controlled location could be specified to be substantially equal to the determined location of the first high-temperature region 454a. Additionally or alternatively, the controlled location could be specified relative to the determined location of the first high-temperature region 454a such that, over a number of subsequent time periods (e.g., subsequent to the first time period), the heating laser 420 could heat, ablate, burn, or otherwise effect a change in a series of target regions of the biological tissue 450. For example, the heating laser 420 could be operated to ablate tissue along a specified trajectory on the surface of the biological tissue 450.

In some examples, the heating laser 420 could be operated as described above to control the orientation of a beam of electromagnetic radiation emitted by the heating laser 420 such that the beam of electromagnetic radiation intersects with the biological tissue 450 proximate to the determined location of a high temperature region of the biological tissue 450 (e.g., first high-temperature region 454a). This could include adjusting the orientation of the beam of electromagnetic radiation emitted by the heating laser 420 a plurality of times per second (i.e., at a specified sampling and/or update rate) such that the beam of electromagnetic radiation intersects with the biological tissue 450 proximate to a determined location of a high temperature region of the biological tissue 450 (i.e., the location of the high temperature region could be determined a plurality of times per second). In some examples, the heating laser 420 could be operated to alter the orientation of the beam of electromagnetic radiation only when a determined distance between a determined location of the high temperature region of the biological tissue 450 and a determined location at which the beam of electromagnetic radiation intersects with the biological tissue 450 exceeds a threshold value. Other methods of operating the heating laser 420, the imager 410, and/or other elements of the active tracking system 400 to determine the location of a high-temperature region of the biological tissue 450 and to direct a beam of electromagnetic radiation emitted by the heating laser 420 toward the determined location of the high temperature region are anticipated.

FIG. 4C illustrates the example active tracking system 400 of FIG. 4A during a second time period. The biological tissue 450 has shifted, deformed, or otherwise changed such that the region of the biological tissue 450 corresponding to the first high-temperature region 454a during the first time period corresponds to the second high-temperature region 454b during the second time period. A second combined beam of electromagnetic radiation 425b is directed toward the biological tissue 450 such that the second combined beam of electromagnetic radiation 425b intersects with the biological tissue 450 at a second target region 452b. The heating laser 420 is oriented in the same direction during the second time period as during the first; as such, the second target region 452b is not collocated with the second high-temperature region 454b of the biological tissue 450. Further, the second combined beam of electromagnetic radiation 425b results in a second illuminated spot 456b on the biological tissue 450.

FIG. 4D illustrates a second example image 470b that could be generated using the imager 410 during the second period of time (i.e., the period of time illustrated in FIG. 4C). The second example image 470b includes a second image of the biological tissue 471b related at least to infrared light received from the biological tissue 450 during the second period of time by the imager 410. The second image of the biological tissue 471b includes an image of the second high-temperature region 474b. A second determined target region 472b represents the location on the second image of the biological tissue 471b corresponding to the second target region 452b. Note that the second determined target region 472b is not a feature of the second image of the biological tissue 471b; however, the second determined target region 472b could be determined based on the location of an image of the second illuminated spot 476b. During the second period of time, the second target region 452b is not within the second high-temperature region 454b; correspondingly, the second determined target region 472b and the second illuminated spot 476b are separate from the second high-temperature region 474b.

The heating laser 420 could be operated, based at least on information (e.g., images) generated by the imager 410, to change the orientation of the second combined beam of electromagnetic radiation 455b such that the second target region 454b is within the second high-temperature region 454b and/or directed toward a controlled location relative to the location of the second high-temperature region 454b. This could include determining the location of the second high-temperature region 454b and/or second target region 452b relative to elements of the active tracking system 400 (e.g., heating laser 420) and/or relative to elements of the second example image 470b (or any other image) generated by the imager 410. In some examples, this could include determining a set of commands (e.g., actuator operations, galvanometer angles, servomotor rotations) based at least on information in the second example image 470b sufficient to change the orientation of the heating laser 420 such that a combined beam of electromagnetic radiation emitted by the heating laser 420 (and second laser disposed thereupon) intersects with the biological tissue 450 proximate to the second high-temperature region 454b. In some examples, this could include operating the heating laser 420 such that the orientation of a beam of electromagnetic radiation emitted by the heating laser 420 changes a small amount during respective time periods (e.g., update periods) of a plurality of time periods such that the location at which the beam of electromagnetic radiation emitted by the heating laser 420 intersects the biological tissue 450 changes incrementally to approach the second high-temperature region 454b. Other methods of operating the heating laser 420, imager 410, and other elements of the active tracking system 400 (e.g., to heat, burn, ablate, or otherwise affect a plurality of regions of the biological tissue 450 along a specified trajectory during a plurality of respective subsequent periods of time) are anticipated.

IV. Example Systems of an Active Tracking System

Figure 5:
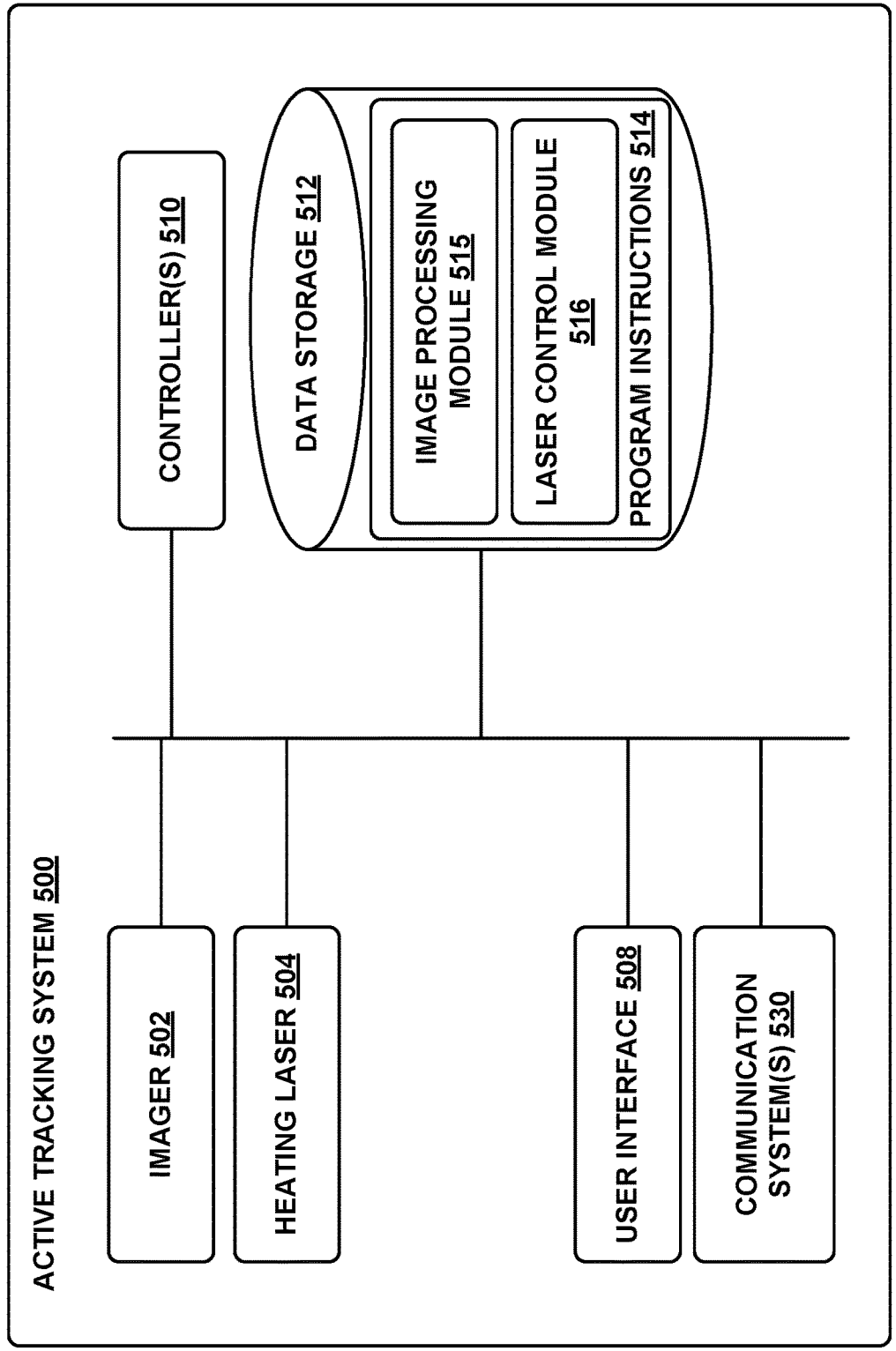
FIG. 5 is a functional block diagram of an example active tracking system.

FIG. 5 is a simplified block diagram illustrating the components of an active tracking system 500, according to an example embodiment. Active tracking system 500 may take the form of or be similar to one of the example active tracking systems 100, 200, 300, 400 shown in FIGS. 1, 2A, 2C, 3A, 3C, 4A, and 4C. However, active tracking system 500 may also take other forms, such as a wall, surgical table, ceiling, or floor-mounted device. Active tracking system 500 could also take the form of a system, device, or combination of devices that is configured to part of another device, apparatus, or system. For example, active tracking system 500 could take the form of an imager, heating laser, and other components configured to be mounted to or otherwise disposed as part of a surgical apparatus, tool, implement, or system (e.g., a robotic surgical system, a stereotactic surgical apparatus, an imaging-guided surgical system). Active tracking system 500 could also take the form of a system configured to image and to emit a heating beam of electromagnetic radiation toward some other industrial environment, medical environment, scientific environment, or some other environment, for example, a work piece to be marked, cut, inscribed, tracked, or otherwise manipulated and/or measured. Active tracking system 500 also could take other forms.

In particular, FIG. 5 shows an example of an active tracking system 500 having an imager 502, a heating laser 504, a user interface 508, communication system(s) 530 for transmitting data to a remote system, and controller(s) 510. The components of the active tracking system 500 may be disposed on or within a mount or housing or on some other structure for mounting the device to enable stable imaging, heating, or other functions relative to elements in an environment of interest, for example, to surgical frame secured relative to a biological tissue of interest.

Controller 510 may include a general-purpose processor or a special purpose processor (e.g., digital signal processors, application specific integrated circuits, etc.). The one or more controllers 510 can be configured to execute computer-readable program instructions 514 that are stored in a computer readable data storage 512 and that are executable to provide the functionality of an active tracking system 500 as described herein.

The computer readable data storage 512 may include or take the form of one or more non-transitory, computer-readable storage media that can be read or accessed by at least one controller 510. The one or more computer-readable storage media can include volatile and/or non-volatile storage components, such as optical, magnetic, organic or other memory or disc storage, which can be integrated in whole or in part with at least one of the one or more controllers 510. In some embodiments, the computer readable data storage 512 can be implemented using a single physical device (e.g., one optical, magnetic, organic or other memory or disc storage unit), while in other embodiments, the computer readable data storage 512 can be implemented using two or more physical devices.

Imager 502 could be any device capable of detecting infrared light received from a biological tissue or from some other environment of interest. The imager 502 could include a variety of components, including infrared sensors, infrared cameras (e.g., a camera configured to image light having a wavelength between approximately 9 micrometers and approximately 14 micrometers), bolometers, microbolometers, focal plane arrays, or other devices and/or arrangements of devices configured to generate an image of an environment of interest by detecting infrared light received from the environment of interest. The imager 502 could be configured and/or operated to determine the temperature of a region of the environment of interest. The imager 502 could include one or more optical elements including but not limited to lenses, apertures, visible-light mirrors, infrared-light mirrors, diffraction gratings, filters (e.g., a filter configured to substantially block visible light while transmitting infrared light), or other optical elements configured to interact with infrared light received from the environment of interest so as to enable imaging of the received infrared light. The imager 502 could additionally be configured to image other objects and/or to detect energy other than infrared light. The imager 502 could be configured to rotate, translate, or otherwise move such that the region imaged by the imager 502 (i.e., a region in the direction of an optical axis of the imager 502) could be controlled and/or changed.

The heating laser 504 could be any device configured to emit a directed beam of electromagnetic radiation sufficient to cause localized heating of a target region of an environment of interest proximate to where the emitted beam intersects with the environment of interest. The heating laser 504 could be a medical laser. The heating laser 504 could include a $CO_2$ laser, a semiconductor diode laser, a dye laser, an excimer laser, a fiber laser, a gas laser, a free electron laser, or some other type or types of laser. The heating laser 504 could include optical elements configured to affect one or more properties of the beam of electromagnetic energy emitted by the heating laser 504, e.g., lenses, mirrors, diffraction gratings, volume holographic gratings, collimators, nonlinear optical elements (e.g., frequency doubling or tripling media), or other elements. The heating laser 504 could be configured such that one or more properties of the beam of electromagnetic energy have a specified value. The heating laser 504 could be configured such that the orientation (i.e., location and/or angular direction) of the emitted beam of electromagnetic energy is controllable. In some examples, this could include rotating, translating, or otherwise moving the heating laser 504. Additionally or alternatively, the heating laser 504 could include optical elements actuated to control the orientation of the emitted beam of electromagnetic energy. Other configurations and methods of controlling the orientation of the emitted beam of electromagnetic energy and/or other properties of the heating laser 504 are anticipated.

The program instructions 514 stored on the computer readable data storage 512 may include instructions to perform any of the methods described herein. For instance, in the illustrated embodiment, program instructions 514 include an image processing module 515 and a laser control module 516.

The image processing module 515 can include instructions for operating the imager 502 and for manipulating information (e.g., infrared images of a target environment) generated by the imager 502. For example, the controller(s) 510 may operate the imager 502 during each of a set of pre-set measurement and/or laser updating periods. In particular, the image processing module 515 can include instructions for locating one or more high-temperature regions within an image of an environment of interest. In some examples, a threshold operation could be applied to a generated image about detected received infrared light from a biological tissue or other environment of interest and circle-fitting or some other centroid-locating operation could be applied to the thresholded data to determine the location of one or more high-temperature regions within the image. Peak detection, wavelet decomposition, fitting of a Gaussian or other distribution, or some other algorithm or combination of algorithms could be employed to determine the presence and/or location of one or more high-temperature regions within an image of a biological tissue or other environment of interest. Further, the image processing module 515 could include instructions to determine a temperature or other information about the one or more high-temperature regions corresponding to the image of the high-temperature region (or corresponding to other regions of an image generated by the imager 502); for example, the amplitude of the detected received infrared light corresponding to a high-temperature region could be used (e.g., using a look-up table or other method) to determine the temperature of the high-temperature region. Such methods could additionally or alternatively be used to determine the temperature or other information (e.g., thermal information, specific heat, thermal conductivity, energy of vaporization) about other regions of an environment imaged by the imager 502.

The laser control module 516 can include instructions for operating the heating laser 504 to enable any of the functions or applications of an active tracking system as described herein. Generally, instructions in the laser control module 516 describe methods of operating the heating laser 504 such that the orientation of an emitted beam of electromagnetic radiation emitted by the heating laser 504 intersects with an environment of interest at a controlled location based on a determined location of a high-temperature region of the environment of interest (e.g., a location determined by the image processing module 514 based on image data generated using the imager 504). Other operations, functions, and applications of the heating laser 504 and/or of other components of the active tracking system 500 as described herein could be implemented as program instructions in the laser control module 516.

Some of the program instructions of the image processing module 515 and/or laser control module 516 may, in some examples, be stored in a computer-readable medium and executed by a processor located external to the active tracking system 500. For example, the active tracking system 500 could be configured to image a biological environment and then transmit the data to a remote server, which may include a mobile device, a personal computer, the cloud, or any other remote system, for further processing.

User interface 508 could include indicators, displays, buttons, touchscreens, and/or other elements configured to present information about the active tracking system 500 to a user and/or to allow the user to operate the active tracking system 500. Additionally or alternatively, the active tracking system 500 could be configured to communicate with another system (e.g., a cellphone, a tablet, a computer, a remote server) and to present elements of a user interface using the remote system. The user interface 508 could be disposed proximate to the heating laser 504, imager, 502, controller(s) 510, or other elements of the active tracking system 500 or could be disposed away from other elements of the active tracking system 500 and could further be in wired or wireless communication with the other elements of the active tracking system 500. The user interface 508 could be configured to allow a user to specify a target region of a biological tissue, specify a temperature to heat the target region to using the heating laser 504, plan a trajectory within a biological tissue to ablate using the heating laser 504, or to specify some other operation, function, or property of operation of the active tracking system 500. The user interface 508 could be configured to present information about a biological tissue (e.g., a temperature, a specific heat, a thermal conductivity) to the user using a display, to present a degree of progress of an ongoing function of the active tracking system (e.g., a degree of progress in ablating biological tissue along a specified trajectory), to present an image of a biological tissue generated using the imager 502 or using some other imaging component or sensor, or to present some other information to a user. Other configurations and methods of operation of a user interface 508 are anticipated.

Communication system(s) 530 may also be operated by instructions within the program instructions 514, such as instructions for sending and/or receiving information via a wireless antenna, which may be disposed on or in the active tracking system 500. The communication system(s) 530 can optionally include one or more oscillators, mixers, frequency injectors, etc. to modulate and/or demodulate information on a carrier frequency to be transmitted and/or received by the antenna. In some examples, the active tracking system 500 is configured to indicate an output from the controller(s) 510 by transmitting an electromagnetic or other wireless signal according to one or more wireless communications standards (e.g., Bluetooth, WiFi, IRdA, ZigBee, WiMAX, LTE). In some examples, the communication system(s) 530 could include one or more wired communications interfaces and the active tracking system 500 could be configured to indicate an output from the controller(s) 510 by operating the one or more wired communications interfaces according to one or more wired communications standards (e.g., USB, FireWire, Ethernet, RS-232).

The computer readable data storage 512 may further contain other data or information, such as medical and health history of a patient whose biological tissue is being tracked or otherwise affected by the active tracking system 500, that may be useful in tracking or otherwise interacting with a biological tissue or other environment of interest. Further, the computer readable data storage 512 may contain data corresponding to imaging information about a biological tissue or other environment of interest. The computer readable data storage 512 may contain calibration data corresponding to a configuration of the active tacking system 500. For example, the computer readable data storage 512 may contain information about the relative location of the imager 502 and the heating laser 504, information describing a model to determine the location of a target region of the heating laser 504 based on the location of a detected image of a high temperature-region of an imaged environment and/or the location of a detected image of some other spot of illumination of an imaged environment. The laser control module 516 may include instructions for generating calibration and/or model data for the active tracking system 500 based on data collected during operation of the active tracking system 500. For example, the laser control module 516 may generate a mapping between locations of target regions in the environment of the active tracking system 500 and locations of images of high-temperature regions of the environment as imaged using the imager 502. Calibration, model, imaging, and/or other data may also be generated by a remote server and transmitted to the active tracking system 500 via communication system(s) 530.

In some examples, the collected calibration and/or model data, stored information about operation of the active tracking system 500 (e.g., information about ablation of biological tissues performed using the active tracking system 500), health state information (e.g., thermal properties of biological tissues) detected by the active tracking system 500 and other usage or other information may additionally be input to a cloud network (e.g., using the communications system(s) 530) and be made available for download by users having sufficient permissions (e.g., a surgeon tasked with reviewing the outcome of a surgical intervention wholly or partially effected using the active tracking system 500). Other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring outcomes of a surgical intervention or other treatment. For example, high-density, real-time data may be collected from a population of device users who have experienced a surgical intervention using the active tracking system 500 to assess the safety and efficacy of the surgical intervention. Such data may also be used on an individual level to assess a particular patient's response to a surgical intervention or therapy. Based on this data, a physician or clinician may be able to tailor a future surgical intervention or other treatment to suit an individual's needs.

V. Illustrative Methods

Figure 6:
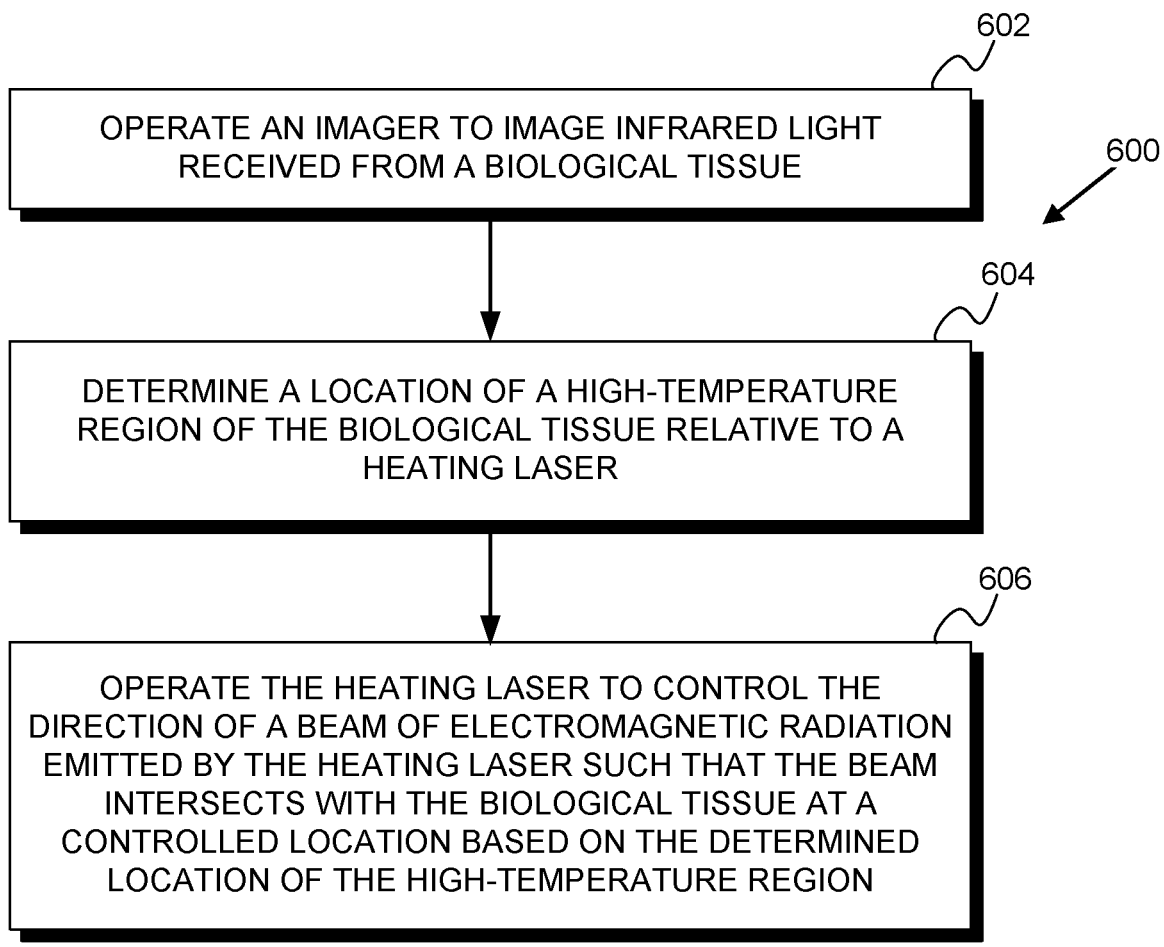
FIG. 6 is a flowchart of an example method.

FIG. 6 is a flowchart of a method 600 for operating elements of an active tracking system to perform functions and/or applications of the active tracking system. The active tracking system includes an imager configured to image a biological tissue by detecting infrared light received from the biological tissue; further, the infrared light received from the biological tissue is related to a temperature of the biological tissue. The active tracking system further includes a heating laser configured to emit a beam of electromagnetic radiation having a controlled orientation (i.e., location and/or angular direction) at the biological tissue; further, the beam of electromagnetic radiation is configured to cause localized heating of a target region of the biological tissue proximate to where the beam of electromagnetic radiation intersects with the biological tissue.

The method 600 includes operating the imager to image infrared light received from the biological tissue 602. This could include powering the imager, initializing the imager (e.g., blanking a memory of the imager, performing a calibration of the imager, providing a stable supply voltage to the imager, setting operational parameters (e.g., exposure time) of the imager), sending a command to the imager to generate an image of the biological tissue, buffering image information from the imager, or some other operation related to generating an image of the biological tissue using the imager. For example, operating the imager to image infrared light received from the biological tissue 602 could include performing image processing on the generated image to remove image artifacts and/or to compensate for inter-pixel variations within an array of sensors of the imager.

The method 600 additionally includes determining a location of a high-temperature region of the biological tissue relative to the heating laser 604. This could include determining the location of an image of the high-temperature region in an image of the biological tissue generated using the imager (602). This could further include combining the determined location of the image of the high-temperature region within the image of the biological tissue with information about the relative locations of the imager, heating laser, and biological tissue to determine the location of the high-temperature region of the biological tissue relative to the heating laser 604. This could include using a model of elements of the active tracking system, using a mapping, using calibration data, and/or using some other algorithm or method.

The method 600 additionally includes operating the heating laser to control the orientation of the emitted beam of electromagnetic radiation emitted by the heating laser such that the beam intersects with the biological tissue at a controlled location based on the determined location of the high-temperature region of the biological tissue 606. This could include determining and executing a set of actuations of the heating laser (e.g., a rotation angle to be executed by a galvanometer or other actuator configured to rotate the heating laser and/or optical elements of the heating laser) such that the beam electromagnetic radiation emitted by the heating laser intersects with the biological environment proximate to the controlled location. In some examples, the controlled location could be substantially equal to the determined location of the high-temperature region of the biological tissue. In some examples, the controlled location could be a specified distance away from the determined location of the high-temperature region in a specified direction such that the heating laser is controlled to heat a sequence of substantially proximate locations of the biological tissue along a specified trajectory at respective specified points in time.

The method 600 could include operating the heating laser to control the power of the emitted beam of electromagnetic radiation by modulating the power of the emitted beam according to one or more determined properties of the biological environment. For example, the power of the emitted beam of electromagnetic radiation could be modulated based on a determined temperature of the high-temperature region of the biological tissue such that the temperature of the high-temperature region is substantially equal to a specified temperature. The specified temperature could be specified to effect some change in the biological temperature; for example, the specified temperature could be a high enough temperature to cause coagulation of blood, denaturation of proteins, vaporization and/or ablation of biological tissue, or some other effect.

The method 600 could further include operating the imager and the heating laser during an initial time period. Operating the imager and heating laser during the initial time period could include operating the heating laser to control the orientation of the beam of electromagnetic radiation such that the beam intersects with the biological tissue at a specified location. In some examples, the specified location could be specified based on information generated by imaging the biological tissue, e.g., by imaging the tissue using fluorescent imaging, a CT scanner, an MMR imager, an ultrasonic scanner, or some other imaging method or apparatus. For example, the active tracking system could be used to image a thermal or other property of the biological tissue (e.g., to generate a map of thermal conductivity of the tissue), and a specified location could be determined based on the imaged property of the biological tissue. In some examples, the specified location could be specified by a beam of electromagnetic radiation emitted by a spotting laser, as described elsewhere herein. Other methods of specifying a specified location and operating an active tracking system relative to the specified location during an initial period are anticipated.

The method 600 could include other additional steps or elements. The method 600 could include any additional steps, or could include details of implementation of the listed steps 602, 604, 606 or of other additional steps, as described herein in relation to the operation of an active tracking system. The method 600 could include determining a thermal property (including but not limited to specific heat, thermal conductivity, and energy of vaporization) of the biological tissue. The steps of the method 600 (e.g., 602, 604, 606) could include determining the locations of two high-temperature regions of the biological tissue and operating the heating laser to emit a beam of electromagnetic radiation having a first orientation toward a first controlled location relative to a determined location of a first high-temperature region of the biological tissue during a first period of time and to emit a beam of electromagnetic radiation having a second orientation toward a second controlled location relative to a determined location of a second high-temperature region of the biological tissue during a second period of time. Additional and alternative steps of the method 600 are anticipated.

In some examples, the environment described in relation to the method 600 above could be a biological tissue of a human body. For example, the environment could be a tissue that has been determined to include a tumor that could be ablated by the controlled application of electromagnetic energy applied, e.g., by an active tracking system as described herein. Other examples of environments, target regions, methods of operating an active tracking system, configurations of active tracking systems, and other elements are anticipated.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, information about a surgical intervention performed on the user, information about biological tissues of a user, a user's preferences, or a user's current location), or to control whether and/or how to receive content from a content server (e.g., a profile of power to ablate a tissue applied using a heating laser) that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a hospital, city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to control the orientation, power, and other aspects of use of a heating laser in heating biological environments of a human body, it is noted that the disclosed devices, systems, and methods can be applied in other contexts as well. For example, active tracking systems configured as disclosed herein may be included as part of other surgical and/or medical imaging apparatus. In some contexts, such a tracking system could be operated to detect one or more properties of a tissue or other element of a human body, possibly in concert with other medical imaging or other sensor apparatus. In another example, an active tracking system could be configured to apply heat to specified elements and/or regions of a non-tissue element of a human body. For example, the active tracking system could be configured and/or applied to apply heat to a specified region of an implantable device (e.g., a stent, an artificial joint, a pacemaker) to effect a desired change in the implantable device (e.g., to section the device, to weld an element of the device, to activate an element of the device, to trim an element (e.g., an electrode) of the device).

In other examples, devices, systems, and methods disclosed herein may be applied to heat specified regions of and/or track thermally-tagged regions of environments that are not in or on a human body. For example, active tracking systems disclosed herein may be included in systems used to apply heat to a specified region (e.g., a tissue of) of an animal. In another example, devices, systems, and methods disclosed herein may be applied to heat specified regions of and/or track thermally-tagged regions of an industrial environment or a work element of an industrial process, such as a work element in a laser cutting process.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   a camera system;
   a heating laser;
   a spotting laser; and
   a controller comprising a memory and at least one processor, wherein the processor is configured to execute instructions stored in the memory so as to perform operations, wherein the operations comprise:
   operating the camera system, during a first time period, to generate a first image of a biological tissue;
   determining, based on the first image of the biological tissue, (i) that the spotting laser illuminated a specified region of the biological tissue during the first time period, and (ii) a location of the specified region relative to the heating laser;
   based on the determined location of the specified region, controlling the heating laser to emit a beam of electromagnetic radiation toward the specified region of the biological tissue to heat the specified region of the biological tissue;
   operating the camera system, during a second time period following the first time period, to generate information indicative of respective temperatures of a plurality of regions of the biological tissue;
   determining, based on the generated information, a heated region from among the plurality of regions of the biological tissue;
   determining a location, relative to the heating laser, of a target region of biological tissue based on a location of the heated region; and
   based on the determined location of the target region of biological tissue, during a third time period following the second time period, controlling the heating laser to emit a beam of electromagnetic radiation toward the target region of biological tissue.

2. The system of claim 1, wherein the spotting laser is configured to emit visible light, and wherein operating the camera system to generate the first image of the biological tissue comprises imaging visible light.

3. The system of claim 1, wherein the spotting laser is configured to emit infrared light, and wherein operating the camera system to generate the first image of the biological tissue comprises generating information indicative of respective temperatures of a plurality of regions of the biological tissue.

4. The system of claim 1, wherein the determined location of the target region is a specified distance away from the location of the heated region in a specified direction.

5. The system of claim 4, wherein the determined location of the target region is a location along a specified trajectory relative to the location of the heated region.

6. The system of claim 1, wherein the determined location of the target region is a specified distance away from the location of the heated region in a specified direction, and wherein the specified distance and specified direction are specified such that the heating laser is controlled to heat a sequence of locations of the biological tissue along a specified trajectory between the location of the heated region and the determined location of the target region at respective specified points in time.

7. The system of claim 1, wherein the operations further comprise:
   modulating a power of the beam of electromagnetic radiation based on a detected temperature of the heated region of biological tissue and a specified temperature.

8. The system of claim 1, wherein the operations further comprise determining a thermal property of the biological tissue using the camera system and the heating laser.

9. The system of claim 1, wherein the camera system comprises a filter that blocks light of wavelengths corresponding to a wavelength of the beam of electromagnetic radiation emitted by the heating laser.

10. The system of claim 1, wherein the camera system can detect infrared light having a wavelength between 9 micrometers and 14 micrometers.

11. The system of claim 1, wherein the camera system has an optical axis, wherein the heating laser has an emitted beam axis, wherein the optical axis is co-axial with the emitted beam axis.

* * * * *